(12) United States Patent
Turkson et al.

(10) Patent No.: US 7,842,671 B1
(45) Date of Patent: Nov. 30, 2010

(54) PEPTIDOMIMETIC INHIBITORS OF STAT ACTIVITY AND USES THEREOF

(75) Inventors: James Turkson, Tampa, FL (US); Richard Jove, Tampa, FL (US); Said M. Sebti, Tampa, FL (US); Andrew D. Hamilton, Guildford, CT (US)

(73) Assignees: University of South Florida, Tampa, FL (US); Yale University, New Haven, CT (US)

( * ) Notice: Subject to any disclaimer, the term of this patent is extended or adjusted under 35 U.S.C. 154(b) by 186 days.

(21) Appl. No.: 11/986,237

(22) Filed: Nov. 19, 2007

Related U.S. Application Data

(63) Continuation of application No. 10/784,309, filed on Feb. 20, 2004, now Pat. No. 7,342,095.

(60) Provisional application No. 60/319,960, filed on Feb. 20, 2003.

(51) Int. Cl.
*A61K 38/00* (2006.01)

(52) U.S. Cl. ..................................................... 514/19

(58) Field of Classification Search ....................... None
See application file for complete search history.

(56) References Cited

U.S. PATENT DOCUMENTS

| 4,179,337 A | 12/1979 | Davis et al. |
|---|---|---|
| 2007/0032418 A1 | 2/2007 | Shapiro et al. |

FOREIGN PATENT DOCUMENTS

| WO | WO 98/12201 A1 | 3/1998 |
|---|---|---|
| WO | WO 00/44774 A2 | 8/2000 |
| WO | WO 0044774 A2 * | 8/2000 |

OTHER PUBLICATIONS

Turkson J, et al, "Phosphotyrosyl peptides block Stat3-mediated DNA binding activity, gene regulation, and cell transformation," J Biol Chem. Nov. 30, 2001;276(48):45443-55, from Applicant's IDS.*
Turkson, J. et al. uPhosphotyrosyl Peptides Block Stat3-mediated DNA Binding Activity, Gene Regulation, and Cell Transformation The Journal of Bio/ogical Chemistry, Nov. 30, 2001, pp. 45443-45455, vol. 276, No. 48.*
Akira, S. "Roles of STAT3 defined by tissue-specific gene targeting" *Oncogene*, 2000, pp. 2607-2611, vol. 19.
Becker, S. et al. "Three-dimensional structure of the Stat3β homodimer bound to DNA" *Nature*, Jul. 9, 1998, pp. 145-151, vol. 394.
Berg, T. et al. "Small-molecule antagonists of Myc/Max dimerization inhibit Myc-induced transformation of chicken embryo fibroblasts" *PNAS*, Mar. 19, 2002, pp. 3830-3835, vol. 99, No. 6.
Bowman, T. et al. "STATs in oncogenesis" *Oncogene*, 2000, pp. 2474-2488, vol. 19.
Bowman, T. et al. "Stat3-mediated Myc expression is required for Src transformation and PDGF-induced mitogenesis" *PNAS*, Jun. 19, 2001, pp. 7319-7324, vol. 98, No. 13.
Bromberg, J. et al. "Stat3 Activation is Required for Cellular Transformation by v-src" *Molecular and Cellular Biology*, May 1998, pp. 2553-2558, vol. 18, No. 5.
Bromberg, J. et al. "The role of STATs in transcriptional control and their impact on cellular function" *Oncogene*, 2000, pp. 2468-2473, vol. 19.
Buettner, R. et al. "Activated STAT Signaling in Human Tumors Provides Novel Molecular Targets for Therapeutic Intervention" *Clinical Cancer Research*, Apr. 2002, pp. 945-954, vol. 8.
Catlett-Falcone, R. et al. "STAT proteins as novel targets for cancer therapy" *Current Opinion in Oncology*, 1999, pp. 490-496, vol. 11.
Catlett-Falcone, R. et al. "Constitutive Activation of Stat3 Signaling Confers Resistance to Apoptosis in Human U266 Myeloma Cells" *Immunity*, Jan. 1999, pp. 105-115, vol. 10.
Chen, X. et al. "Crystal Structure of a Tyrosine Phosphorylated STAT-1 Dimer Bound to DNA" *Cell*, May 29, 1998, pp. 827-839, vol. 93.
Darnell, J. E., Jr. "STATs and Gene Regulation" *Science*, Sep. 12, 1997, pp. 1630-1635, vol. 277.
Darnell, J. E., Jr. "Transcription Factors As Targets for Cancer Therapy" *Nat. Rev. Cancer*, Oct. 2002, pp. 740-749, vol. 2.
Epling-Burnette, P. K. et al. "Inhibition of STAT3 signaling leads to apoptosis of leukemic large granular lymphocytes and decreased Mcl-1 expression" *The Journal of Clinical Investigation*, Feb. 2001, pp. 351-361, vol. 107, No. 3.
Frank, D. A. "STAT Signaling in the Pathogenesis and Treatment of Cancer" *Molecular Medicine*, 1999, pp. 432-456, vol. 5.
Garcia, R. et al. "Constitutive Activation of Stat3 in Fibroblasts Transformed by Diverse Oncoproteins and in Breast Carcinoma Cells" *Cell Growth & Differentiation*, Dec. 1997, pp. 1267-1276, vol. 8.
Garcia, R. et al. "Activation of STAT Transcription Factors in Oncogenic Tyrosine Kinase Signaling" *Journal of Biomedical Science*, 1998, pp. 79-85, vol. 5.
Garcia, R. et al. "Constitutive activation of Stat3 by the Src and JAK tyrosine kinases participates in growth regulation of human breast carcinoma cells" *Oncogene*, 2001, pp. 2499-2513, vol. 20.
Gibson, B. W. et al. "Liquid Secondary Ionization Mass Spectrometric Characterization of Two Synthetic Phosphotyrosine-Containing Peptides" *J. Am. Chem. Soc.*, 1987, pp. 5343-5348, vol. 109.
Gouilleux, F. et al. "Prolactin and Interleukin-2 Receptors in T Lymphocytes Signal through a MGF-STAT5-Like Transcription Factor" *Endocrinology*, 1995, pp. 5700-5708, vol. 136, No. 12.

(Continued)

*Primary Examiner*—Cecilia Tsang
*Assistant Examiner*—Thomas S Heard
(74) *Attorney, Agent, or Firm*—Saliwanchik, Lloyd & Saliwanchik

(57) ABSTRACT

The subject invention concerns compositions and methods for blocking cancer cell growth or proliferation and/or inducing cancer cell death. Compositions of the present invention are peptidomimetics that inhibit STAT function. Peptidomimetics of the invention include compounds of the formula RY*L (where Y* represents phosphotyrosine), with the R group at the Y-1 position. Peptidomimetics of the invention disrupt Stat3 activation and function. Peptidomimetics of the invention significantly inhibit tumor cell growth and induce tumor cell death.

17 Claims, 9 Drawing Sheets
(1 of 9 Drawing Sheet(s) Filed in Color)

OTHER PUBLICATIONS

Grandis, J. R. at al. "Constitutive activation of Stat3 signaling abrogates apoptosis in squamous cell carcinogenesis in vivo" *PNAS*, Apr. 11, 2000, pp. 4227-4232, vol. 97, No. 8.

Hirano, T. et al. "Roles of STAT3 in mediating the cell growth, differentiation and survival signals relayed through the IL-6 family of cytokine receptors" *Oncogene*, 2000, pp. 2548-2556, vol. 19.

Horvath, C. M. "STAT proteins and transcriptional responses to extracellular signals" *TIBS*, Oct. 2000, pp. 496-502, vol. 25.

Johnson, P. J. et al. "Overexpressed pp60c-src Can Induce Focus Formation Without Complete Transformation of NIH 3T3 Cells" *Molecular and Cellular Biology*, May 1985, pp. 1073-1083, vol. 5, No. 5.

Jones, G. et al. "Development and Validation of a Genetic Algorithm for Flexible Docking" *J. Mol. Biol.*, 1997, pp. 727-748, vol. 267.

Kitas, E. A. et al. "Synthesis of O-Phosphotyrosine-Containing Peptides. 3. Synthesis of H-Pro-Try(P)-Val-OH via Dimethyl Phosphate Protection and the Use of Improved Deprotection Procedures" *J. Org. Chen.*, 1990, pp. 4181-4187, vol. 55.

Kotenko, S. V. et al. "Jak-Stat signal transduction pathway through the eyes of cytokine class II receptor complexes" *Oncogene*, 2000, pp. 2557-2565, vol. 19.

Lin, T. S. et al. "STAT signaling in the pathogenesis and treatment of leukemias" *Oncogene*, 2000, pp. 2496-2504, vol. 19.

Lin, J. et al. "The role of Stat5a and Stat5b in signaling by IL-2 family cytokines" *Oncogene*, 2000, pp. 2566-2576, vol. 19.

Merrifield R. B. "Solid Phase Peptide Synthesis. I. The Synthesis of a Tetrapeptide" *Am. Chem. Soc.*, Jul. 20, 1963, pp. 2149-2152, vol. 85.

Rojas, M. et al. "Genetic engineering of proteins with cell membrane permeability" *Nature Biotechnology*, Apr. 1998, pp. 370-375, vol. 16.

Sasse, J. et al. "Mutational Analysis of Acute-Phase Response Factor/Stat3 Activation and Dimerization" *Molecular and Cellular Biology*, Aug. 1997, pp. 4677-4686, vol. 17, No. 8.

Schindler, C. et al. "Transcriptional Responses to Polypeptide Ligands: The JAK-STAT Pathway" *Annu. Rev. Biochem.*, 1995, pp. 621-651, vol. 64.

Seidel, H. M. et al. "Spacing of palindromic half sites as a determinant of selective STAT (signal transducers and activators of transcription) DNA binding and transcriptional activity" *Proc. Natl. Acad. Sci. USA*, Mar. 2, 1995, pp. 3041-3045, vol. 92.

Seidel, H. M. et al. "Pharmaceutical intervention in the JAK/STAT signaling pathway" *Oncogene*, 2000, pp. 2645-2656, vol. 19.

Shuai, K. et al. "A Single Phosphotyrosine Residue of Stat91 Required for Gene Activation by Interferon-γ" *Science*, Sep. 24, 1993, pp. 1744-1746, vol. 261.

Shuai, K. et al. "Interferon Activation of the Transcription Factor Stat91 Involves Dimerization through SH2-Phosphotyrosyl Peptide Interactions" *Cell*, Mar. 11, 1994, pp. 821-828, vol. 76.

Smithgall, T. E. et al. "Control of myeloid differentiation and survival by Stats" *Oncogene*, 2000, pp. 2612-2618, vol. 19.

Song, J. I. et al. "STAT signaling in head and neck cancer" *Oncogene*, 2000, pp. 2489-2495, vol. 19.

Song, L. et al. "Activation of Stat3 by receptor tyrosine kinases and cytokines regulates survival in human non-small cell carcinoma cells" *Oncogene*, 2003, pp. 4150-4165, vol. 22.

Stark, G. R. et al. "How Cells Respond to Interferons" *Annu. Rev. Biochem.*, 1998, pp. 227-264, vol. 67.

Turkson, J. et al. "Stat3 Activation by Src Induces Specific Gene Regulation and Is Required for Cell Transformation" *Molecular and Cellular Biology*, May 1998, pp. 2545-2552, vol. 18, No. 5.

Turkson, J. et al. "Requirement for Ras/Rac1-Mediated p38 and c-Jun N-Terminal Kinase Signaling in Stat3 Transcriptional Activity Induced by the Src Oncoprotein" *Molecular and Cellular Biology*, Nov. 1999, pp. 7519-7528, vol. 19, No. 11.

Turkson, J. et al. "STAT proteins: novel molecular targets for cancer drug discovery" *Oncogene*, 2000, pp. 6613-6626, vol. 19.

Turkson, J. et al. "Phosphotyrosyl Peptides Block Stat3-mediated DNA Binding Activity, Gene Regulation, and Cell Transformation" *The Journal of Biological Chemistry*, Nov. 30, 2001, pp. 45443-45455, vol. 276, No. 48.

Wagner, B. et al. "The SIF binding element confers *sis*/PDGF inducibility onto the *c-fos* promoter" *The EMBO Journal* 1990, pp. 4477-4484, vol. 9, No. 13.

Yamauchi, K. et al. "Phosphatidylinositol 3-Kinase Functions Upstream of Ras and Raf in Mediating Insulin Stimulation of *c-fos* Transcription*" *The Journal of Biological Chemistry*, Jul. 15, 1993, pp. 14597-14600, vol. 268, No. 20.

Yu, C. et al. "Enhanced DNA-Binding Activity of a Stat3-Related Protein in Cells Transformed by the Src Oncoprotein" *Science*, Jul. 7, 1995, pp. 81-83, vol. 269.

Zhang, Y. et al. "Activation of Stat3 in v-Src-transformed Fibroblasts Requires Cooperation of Jak1 Kinase Activity" *The Journal of Biological Chemistry*, Aug. 11, 2000, pp. 24935-24944, vol. 275, No. 32.

Posternak, T. et al. "De la protection contre l'hydrolyse enzymatique exercée par les groupes phosphoryles II." *Helv. Chim. Acta.*, 1945, pp. 1258-1270, vol. 28.

Waldmann, H. et al. "New Enzymatic Protecting Group Techinique for the Construction of Peptides and Glycopeptides," *Biomedica Biochimica Acta*, 1991, pp. S243-S248, vol. 50 (10-11).

* cited by examiner

SEQUENCE LISTING

```
<160> NUMBER OF SEQ ID NOS: 6

<210> SEQ ID NO 1
<211> LENGTH: 18
<212> TYPE: PRT
<213> ORGANISM: Artificial sequence
<220> FEATURE:
<223> OTHER INFORMATION: murine
<220> FEATURE:
<221> NAME/KEY: MISC_FEATURE
<222> LOCATION: (2)..(2)
<223> OTHER INFORMATION: phosphorylation of tyrosine

<400> SEQUENCE: 1

Pro Xaa Leu Lys Thr Lys Ala Ala Val Leu Leu Pro Val Leu Leu Ala
1               5                   10                  15

Ala Pro

<210> SEQ ID NO 2
<211> LENGTH: 18
<212> TYPE: PRT
<213> ORGANISM: Artificial sequence
<220> FEATURE:
<223> OTHER INFORMATION: murine
```

```
<400> SEQUENCE: 2

Pro Tyr Leu Lys Thr Lys Ala Ala Val Leu Leu Pro Val Leu Leu Ala
1               5                   10                  15

Ala Pro

<210> SEQ ID NO 3
<211> LENGTH: 24
<212> TYPE: DNA
<213> ORGANISM: Artificial sequence
<220> FEATURE:
<223> OTHER INFORMATION: murine

<400> SEQUENCE: 3
agcttcattt cccgtaaatc ccta                                          24

<210> SEQ ID NO 4
<211> LENGTH: 18
<212> TYPE: DNA
<213> ORGANISM: Artificial sequence
<220> FEATURE:
<223> OTHER INFORMATION: bovine

<400> SEQUENCE: 4
agatttctag gaattcaa                                                 18

<210> SEQ ID NO 5
<211> LENGTH: 6
<212> TYPE: PRT
<213> ORGANISM: Artificial sequence
<220> FEATURE:
<223> OTHER INFORMATION: murine
<220> FEATURE:
<221> NAME/KEY: MISC_FEATURE
<222> LOCATION: (2)..(2)
<223> OTHER INFORMATION: phosphorylation of tyrosine

<400> SEQUENCE: 5

Pro Xaa Leu Lys Thr Lys
1               5

<210> SEQ ID NO 6
<211> LENGTH: 6
<212> TYPE: PRT
<213> ORGANISM: Artificial sequence
<220> FEATURE:
<223> OTHER INFORMATION: murine
<220> FEATURE:
<221> NAME/KEY: MISC_FEATURE
<222> LOCATION: (4)..(4)
<223> OTHER INFORMATION: phosphorylation of tyrosine

<400> SEQUENCE: 6

Ala Ala Pro Xaa Leu Lys
1               5
```

US 7,842,671 B1

PEPTIDOMIMETIC INHIBITORS OF STAT ACTIVITY AND USES THEREOF

CROSS-REFERENCE TO RELATED APPLICATION

The application is a continuation application of U.S. application Ser. No. 10/784,309, filed Feb. 20, 2004 now U.S. Pat. No. 7,342,095, which claims priority to U.S. Provisional Application Ser. No. 60/319,960, filed Feb. 20, 2003, which is hereby incorporated by reference in its entirety, including all figures, nucleic acid sequences, amino acid sequences, and tables.

This invention was made with government support under National Cancer Institute grants CA78038 and CA55652. The government has certain rights in the invention.

FIELD OF INVENTION

This invention relates to materials and methods for blocking tumor growth and inducing tumor cell death by disrupting the activity of a STAT transcription factor protein, such as Stat3.

BACKGROUND OF THE INVENTION

Knowledge of the molecular basis of cancer potentially expands the number of strategies to target cancer cells for therapy. Multiple genetic alterations in cancer frequently result in aberrations in the biochemical properties of signaling molecules, leading to dysregulation of signal transduction mechanisms in tumors and consequently malignant progression. As distinct molecular features of tumors compared to normal cells, these molecular changes conceptually provide unique targets for the design of tumor-selective drugs.

Signal Transducer and Activator of Transcription (STAT) proteins are latent cytoplasmic transcription factors that are activated in response to cytokines and growth factors and consequently regulate cellular processes, including proliferation, differentiation and survival (Darnell, J. E., Jr. (2002); Horvath, C. M. (2000); Darnell, J. E., Jr. (1997); Schindler, C. and Darnell, J. E., Jr. (1995); Bromberg, J. and Darnell, J. E., Jr. (2000); Stark, G. R. et al. (1998); Smithgall, T. E. et al. (2000); Akira, S. (2000); Hirano, T. et al. (2000); Kotenko, S. V. and Pestka, S. (2000)). STAT activation is dependent on tyrosine phosphorylation, which induces dimerization via reciprocal phosphotyrosine (pTyr)-SH2 interactions between two STAT monomers and is required for binding to specific DNA response elements (Shuai, K. et al. (1993); Shuai, K. et al. (1994); Sasse, J. et al. (1997)).

A large number of studies on persistent activation of specific STAT family members, particularly Stat3, have established a strong link to growth and survival of transformed and tumor cells (Bowman, T. et al. (2000a); Catlett-Falcone, R. et al. (1999a); Garcia, R. and Jove, R. (1998); Turkson, J. and Jove, R. (2000); Song, J. I. and Grandis, J. R. (2000); Lin, T. S. et al. (2000)). In a number of human solid and hematological tumors, studies have identified a high frequency of abnormal activation of Stat3. In many tumor cells harboring persistent Stat3 activity, inhibition of Stat3 signaling induces growth arrest and apoptosis. The critical role of Stat3 in the molecular pathogenesis of many diverse tumors provides validation for its targeting in cancer drug discovery (Turkson, J. and Jove, R. (2000); Buettner, R. et al. (2002)).

BRIEF SUMMARY OF THE INVENTION

The subject invention concerns compositions and methods for blocking cancer cell growth or proliferation and/or inducing cancer cell death. Compositions of the present invention are peptidomimetics that inhibit STAT function. Peptidomimetics of the invention include compounds of the formula RY*L (where Y* represents phosphotyrosine), with the R group at the Y-1 position. Peptidomimetics of the invention disrupt Stat3 activation and function. Consistent with their activity of inhibiting Stat3, representative peptidomimetics of the invention significantly inhibit tumor cell growth and induce tumor cell death.

BRIEF DESCRIPTION OF THE DRAWINGS

The file of this patent contains at least one drawing executed in color. Copies of this patent with the color drawing will be provided by the Patent and Trademark Office upon request and payment of the necessary fee.

FIG. 1A shows Stat1 and Stat3 binding to hSIE probe (SEQ ID NO. 3), and FIG. 1B shows Stat1 and Stat5 binding to MGFe probe (SEQ ID NO. 4). Positions of STAT:DNA complexes in gel are labeled. Control lanes represent nuclear extracts from NIH3T3 cells stimulated with EGF but not treated with peptidomimetics.

FIGS. 3A and 3B show luciferase activities in extracts prepared from peptidomimetic designated ISS 610- or ISS 610NP-treated v-Src-transformed mouse fibroblasts that stably express Stat3-dependent (NIH3T3/v-Src/pLucTKS3) and Stat3-independent (NIH3T3/v-Src/pRLSRE) luciferase reporters. Values are the means and S.D. of three independent assays. FIGS. 3C-3E show EMSA analyses of Stat3 DNA-binding activities (using hSIE oligonucleotide probe) (SEQ ID NO. 3) in nuclear extracts prepared from v-Src-transformed NIH3T3/v-Src (FIGS. 3C and 3D), human breast carcinoma MDA-MB-435, MDA-MB-468, and MDA-MB-231 (FIG. 3E). FIG. 3F shows the effect of ISS 610 peptidomimetic on soft-agar growth of v-Src-transformed fibroblasts (NIH3T3/v-Src) and their v-Ras-transformed counterparts (NIH3T3/v-Ras). Transformed cells were seeded in soft agar and treated every 2-3 days with or without 1 mM ISS 610 peptidomimetic until large colonies were evident. Values are the mean and S.D. of the three independent assays.

BRIEF DESCRIPTION OF THE SEQUENCES

Figure 1A:
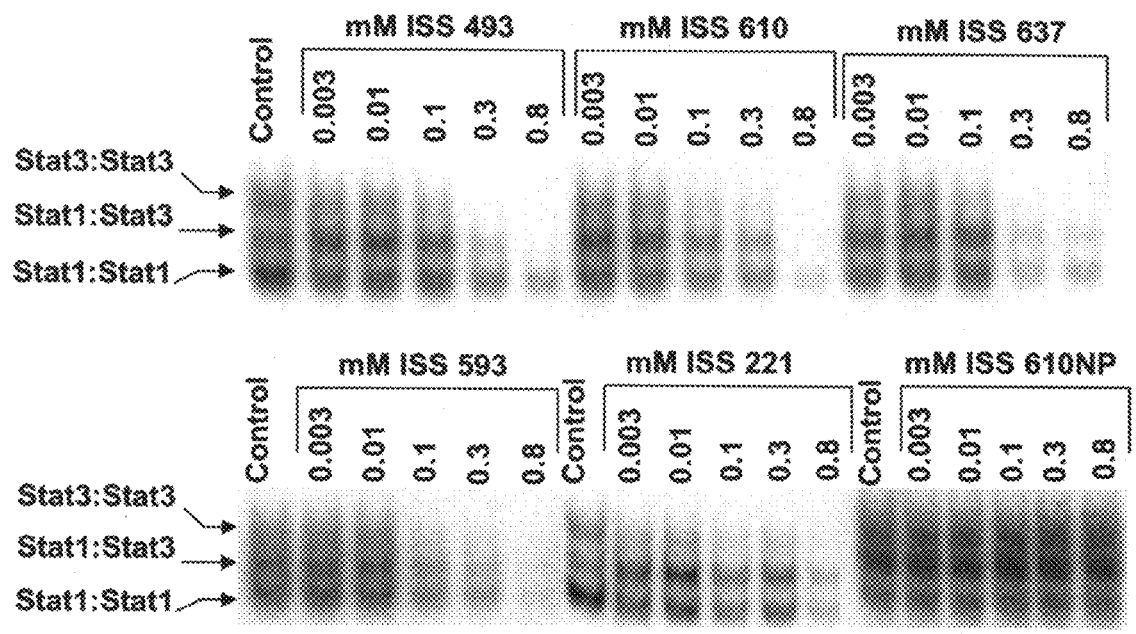
FIGS. 1A and 1B show electrophoretic mobility shift assay (EMSA) analyses of STAT DNA-binding activities showing effects of peptidomimetics. Nuclear extracts containing activated Stat1, Stat3 and Stat5 are treated with the indicated concentrations of peptidomimetics designated ISS 493, ISS 610, ISS 637, ISS 593, ISS 221, or ISS 610NP for 30 min at room temperature prior to incubation with radiolabeled oligonucleotide probes.

SEQ ID NO: 1 is a peptide comprising a membrane translocating sequence.

SEQ ID NO: 2 is a peptide comprising a membrane translocating sequence.

SEQ ID NO: 3 is an oligonucleotide probe designated as hSIE that binds to STAT proteins.

SEQ ID NO: 4 is an oligonucleotide probe designated as MGFe that binds to STAT proteins.

SEQ ID NO: 5 is a peptide.

SEQ ID NO: 6 is a peptide.

DETAILED DISCLOSURE OF THE INVENTION

The subject invention concerns compositions for blocking cancer cell growth or proliferation and/or inducing cancer cell death. Compositions of the invention comprise peptidomimetic molecules that are inhibitors of STAT proteins. Peptidomimetics within the scope of the invention include peptidomimetics having the structure R—Y*L, where R is bound via the Y-1 position and is an organic group as defined herein and Y* is a phosphotyrosine.

In one embodiment, a peptidomimetic of the invention has the structure shown in formula I:

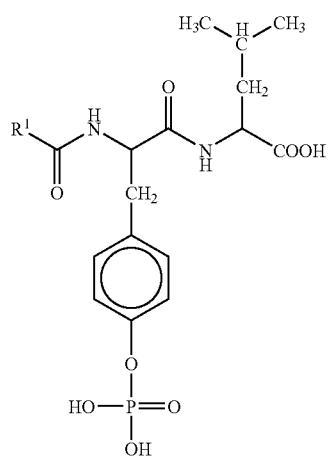

(I)

wherein $R^1$ is alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO$_2$, —NH$_2$, —N-alkyl, alkyl including —CH$_3$, alkoxy including —OCH$_3$, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl;

or a salt thereof.

In a preferred embodiment, peptidomimetics of the invention have an $R^1$ group selected from phenyl, pyridyl, and pyrazinyl moieties. In one embodiment, $R^1$ is phenyl optionally substituted with one or more halogen, —NO$_2$, —CN or —OCH$_3$. In an exemplified embodiment, $R^1$ is phenyl substituted with —OCH$_3$ or —CN. In another embodiment, $R^1$ is pyridyl optionally substituted with one or more halogen or —CH$_3$. In an exemplified embodiment, $R^1$ is pyridyl substituted with Cl and F.

As used herein, alkyl means straight or branched chain, saturated or mono- or polyunsaturated hydrocarbon groups having from 1 to 20 carbon atoms and $C_{1-X}$ alkyl means straight or branched chain alkyl groups containing from one up to X carbon atoms wherein X is any positive integer. For example, $C_{1-6}$ alkyl means straight or branched chain alkyl groups containing from one up to 6 carbon atoms. Alkoxy means an alkyl-O-group in which the alkyl group is as previously described. Cycloalkyl includes a nonaromatic monocyclic or multicyclic ring system, including fused and spiro rings, of from about three to about 10 carbon atoms. A cyclic alkyl may optionally be partially unsaturated. Cycloalkoxy means a cycloalkyl-O-group in which cycloalkyl is as defined herein. Aryl means an aromatic monocyclic or multicyclic carbocyclic ring system, including fused and spiro rings, containing from about six to about 14 carbon atoms. Aryloxy means an aryl-O-group in which the aryl group is as described herein. Alkylcarbonyl means a RC(O)— group where R is an alkyl group as previously described. Alkoxycarbonyl means an ROC(O)— group where R is an alkyl group as previously described. Cycloalkylcarbonyl means an RC(O)— group where R is a cycloalkyl group as previously described. Cycloalkoxycarbonyl means an ROC(O)— group where R is a cycloalkyl group as previously described.

Heteroalkyl means a straight or branched-chain having from one to 20 carbon atoms and one or more heteroatoms selected from nitrogen, oxygen, or sulphur, wherein the nitrogen and sulphur atoms may optionally be oxidized, i.e., in the form of an N-oxide or an S-oxide. Heterocycloalkyl means a monocyclic or multicyclic ring system (which may be saturated or partially unsaturated), including fused and spiro rings, of about five to about 10 elements wherein one or more of the elements in the ring system is an element other than carbon and is selected from nitrogen, oxygen, silicon, or sulphur atoms. Heteroaryl means a five to about a 14-membered aromatic monocyclic or multicyclic hydrocarbon ring system, including fused and spiro rings, in which one or more of the elements in the ring system is an element other than carbon and is selected from nitrogen, oxygen, silicon, or sulphur and wherein an N atom may be in the form of an N-oxide. Arylcarbonyl means an aryl-CO-group in which the aryl group is as described herein. Heteroarylcarbonyl means a heteroaryl-CO-group in which the heteroaryl group is as described herein and heterocycloalkylcarbonyl means a heterocycloalkyl-CO-group in which the heterocycloalkyl group is as described herein. Aryloxycarbonyl means an ROC(O)- group where R is an aryl group as previously described. Heteroaryloxycarbonyl means an ROC(O)— group where R is a heteroaryl group as previously described. Heterocycloalkoxy means a heterocycloalkyl-O— group in which the heterocycloalkyl group is as previously described. Heterocycloalkoxycarbonyl means an ROC(O)— group where R is a heterocycloalkyl group as previously described.

Examples of saturated alkyl groups include, but are not limited to, methyl, ethyl, N-propyl, isopropyl, N-butyl, tert-butyl, isobutyl, sec-butyl, N-pentyl, N-hexyl, N-heptyl, and N-octyl. An unsaturated alkyl group is one having one or more double or triple bonds. Unsaturated alkyl groups include, for example, ethenyl, propenyl, butenyl, hexenyl, vinyl, 2-propynyl, 2-isopentenyl, 2-butadienyl, ethynyl, 1-propynyl, 3-propynyl, and 3-butynyl. Cycloalkyl groups include, for example, cyclopentyl, cyclohexyl, 1-cyclohexenyl, 3-cyclohexenyl, and cycloheptyl. Heterocycloalkyl groups include, for example, 1-piperidinyl, 2-piperidinyl, 3-piperidinyl, 3-morpholinyl, 4-morpholinyl, tetrahydrofuran-2-yl, tetrahydrofuran-3-yl, tetrahydrothien-2-yl, tetrahydrothien-3-yl, 1-piperazinyl, 2-piperazinyl, and 1,4-diazabicyclooctane. Aryl groups include, for example, benzyl, phenyl, indenyl, biphenyl, 1-naphthyl, 2-naphthyl, anthracenyl, and phenanthracenyl. Heteroaryl groups include, for example, 1-pyrrolyl, 2-pyrrolyl, 3-pyrrolyl, furyl, thienyl, imidazolyl, oxazolyl, isoxazolyl, thiazolyl, pyrazolyl, pyridyl, pyrimidyl, purinyl, indolyl, quinolinyl, isoquinolinyl, benzoquinolinyl, carbazolyl, and diazaphenanthrenyl.

As used herein, halogen means the elements fluorine (F), chlorine (Cl), bromine (Br), and iodine (I).

The subject invention also concerns compositions comprising a peptidomimetic of the invention, or a salt thereof, in a pharmaceutically acceptable carrier or diluent.

Figure 5:
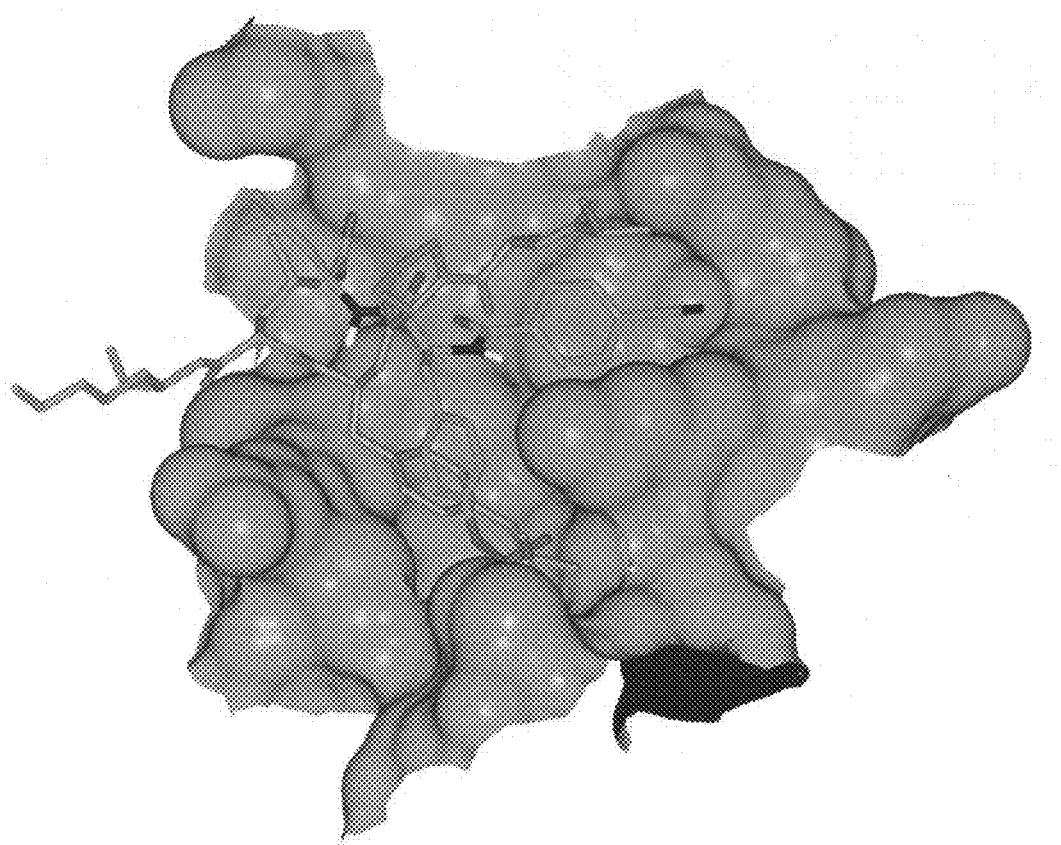
FIG. 5 shows computer modeling of peptidomimetic ISS 610 bound to SH2 pocket. Comparison of the lowest energy GOLD (Jones et al. (1997)) docked conformation of ISS 610 (green), and the C-terminal phosphotyrosine peptide, AAPY*LK (SEQ ID NO. 6), of the associated Stat3β monomer as determined from the crystal structure (orange), in the SH2 binding domain of Stat3β (pale blue) (Becker, S., et al. (1998)).

Examples of peptidomimetics of the invention are shown in Table 3 and have been designated with an "ISS" number. Peptidomimetics of the invention, such as those exemplified herein and designated as ISS 221, ISS 437, ISS 593, ISS 610 and ISS 637 are potent disrupters of active Stat3 and effectively disrupt and dissociate active Stat3:Stat3 dimers. Shown in FIG. 5 is the lowest energy GOLD docked conformation of peptidomimetics ISS 610 in the SH2 domain of Stat3β, as compared to the observed SH2 domain-bound phosphopeptide AAPY*LK (SEQ ID NO. 6) of the associated monomer of Stat3β in the X-ray crystal structure (Becker, S., et al. (1998). The modeling by GOLD flexible docking program reveals that ISS 610 has access to the hydrophobic pocket and available hydrogen bonding interactions on the protein surface. R substituents of formula I include 4-cyanobenzoate (ISS 610), 2,6-dimethoxybenzoate (ISS 637), 2-methylpyridine-3-carboxylic acid (ISS 221), 2,6-dichloro-4-fluoro pyridine-3-carboxylic acid (ISS 593) as well as 5-methylpyrazine carboxylic acid (ISS 493). While peptidomimetics with pyrazinyl or phenyl substitutions are generally more selective for Stat3, the selectivity of these peptidomimetics may be influenced by the presence and the type, as well as the positioning, of functional groups on the aromatic ring.

Salts of the peptidomimetics of the invention include those which are prepared with acids or bases, depending on the particular substituents present on the subject peptidomimetics described herein. Examples of a base addition salts include sodium, potassium, calcium, ammonium, or magnesium salt. Examples of acid addition salts include hydrochloric, hydrobromic, nitric, phosphoric, carbonic, sulphuric, and organic acids like acetic, propionic, benzoic, succinic, fumaric, mandelic, oxalic, citric, tartaric, maleic, and the like. Salts of platinum complexes of the invention can be prepared using conventional techniques.

Peptides of the invention can be readily prepared using standard techniques known in the art, including chemical synthesis (Merrifield, 1963) and genetic engineering. Peptidomimetics of the invention can be synthesized or prepared from peptides using standard chemical procedures and materials.

Peptidomimetics having substitution of amino acids other than those specifically exemplified in the subject peptidomimetics are also contemplated within the scope of the present invention. For example, non-natural amino acids can be substituted for the amino acids of a peptidomimetic of the invention, so long as the peptidomimetic having substituted amino acid(s) retains substantially the same activity as the peptidomimetic in which amino acid(s) have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ϵ-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Table 1 below provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Conservative substitutions whereby a peptidomimetic having an amino acid of one class is replaced with another amino acid of the same class fall within the scope of the subject invention so long as the peptidomimetic having the substitution still retains substantially the same biological activity as a peptidomimetic that does not have the substitution. Thus, peptidomimetics of the invention having the structure $R^1Y*L$ (wherein $R^1$ is as defined herein) include those where the leucine (L) residue is replaced with a nonpolar amino acid, such as valine, alanine, etc. Also specifically contemplated within the scope of the invention are compounds of formula $R^1Y*L$ having analogs of $Y*$ or L wherein the peptidomimetic having the analog has substantially the same biologically activity as a non-analog peptidomimetic. For example, analogs of $Y*$ include those where the aromatic ring of phosphotyrosine can be substituted with various substituents including, but not limited to, any halogen, —OH, —NO$_2$, —NH$_2$, —COOH, alkyl (such as —CH$_3$), and alkoxy (such as —OCH$_3$).

Single letter amino acid abbreviations are defined in Table 2.

TABLE 2

| Letter Symbol | Amino Acid |
| --- | --- |
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |
| Q | Glutamine |
| R | Arginine |
| S | Serine |
| T | Threonine |
| V | Valine |
| W | Tryptophan |
| Y | Tyrosine |
| Z | Glutamine or glutamic acid |

The subject invention also concerns methods for inhibiting the growth or replication of a cell having abnormal growth or replication or whose growth or replication is uncontrolled, such as a cancer cell. In one embodiment, methods of the invention comprise inhibiting function of a STAT by contacting a cell expressing a STAT with a peptidomimetic of the invention wherein the peptidomimetic is taken in or otherwise provided inside the cell. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

Methods of the invention also comprise inhibiting the function and/or growth and replication of a cell that is aberrantly or constitutively expressing a STAT, such as Stat3. In one embodiment, the method comprises contacting a cell with a peptidomimetic of the invention. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

The subject invention also concerns methods for inducing apoptosis in a target cell. In one embodiment, the method comprises contacting a cell with a peptidomimetic of the invention. In one embodiment, the cell is a tumor cell, cancer cell, or a transformed cell. The cell can be a cell from a mammal, including human, dog, cat, and horse. The types of cells encompassed within the scope of the invention include, but are not limited to, cells of breast, kidney, mouth, larynx, esophagus, stomach, testis, cervix, head, neck, colon, ovary, lung, bladder, skin, muscle, pancreas, prostate, bone, eye, blood cells, and brain.

Peptidomimetics of the invention can be delivered to a cell either through direct contact with the cell or via a carrier means. Carrier means for delivering compositions to cells are known in the art and include encapsulating the composition in a liposome moiety, and attaching the platinum complexes to a protein or nucleic acid that is targeted for delivery to the target cell. Published U.S. Patent Application Nos. 20030032594 and 20020120100 disclose amino acid sequences that can be coupled to a composition and that allows the composition to be translocated across biological membranes. Published U.S. Patent Application No. 20020035243 also describes compositions for transporting biological moieties across cell membranes for intracellular delivery.

The subject invention also concerns methods for treating tumors and oncological disorders in a patient. In one embodiment, an effective amount of a peptidomimetic of the present invention is administered to a patient having an oncological disorder and who is in need of treatment thereof. The patient can be a human or other mammal, such as a primate (monkey, chimpanzee, ape, etc.), dog, cat, cow, pig, or horse, or other animals having an oncological disorder. Means for administering and formulating a peptidomimetic for administration to a patient are known in the art, examples of which are described herein. Oncological disorders that can be treated using the subject invention include cancer and/or tumors of the breast, kidney, mouth, larynx, esophagus, stomach, testis, cervix, head, neck, colon, ovary, lung, bladder, skin, muscle, pancreas, prostate, bone, eye, blood cells, and brain. The peptidomimetics of the invention can also be used to treat other disorders that are associated with aberrant or constitutive expression of a STAT, such as Stat3.

For the treatment of tumors and oncological disorders, the peptidomimetics of this invention can be administered to a patient in need of treatment alone, or in combination with other antitumor or anticancer substances and/or with radiation therapy and/or with surgical treatment to remove a tumor or cancerous tissue. These other substances or radiation treatments may be given at the same or different times as the peptidomimetics of this invention. For example, the peptidomimetics of the present invention can be used in combination with mitotic inhibitors such as taxol or vinblastine, alkylating agents such as cisplatin, cyclophosphamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other drugs or antibodies that inhibit cancer cells, such as, for example, GLEEVEC (Novartis) and HERCEPTIN (Genetech), respectively.

Therapeutic application of the subject peptidomimetics, and compositions containing them, can be accomplished by any suitable therapeutic method and technique presently or prospectively known to those skilled in the art. The peptidomimetics can be administered by any suitable route known in the art including, for example, topical, oral, nasal, rectal, parenteral, subcutaneous, intramuscular, or intravenous routes of administration. Administration of the peptidomimetics of the invention can be continuous or at distinct intervals as can be readily determined by a person skilled in the art. The dosage to be administered to a patient can vary depending on several factors, including age, weight, and sex of the patient, and the type and severity of the disease. The ordinarily skilled clinician can determine suitable dosages following evaluation of the patient.

Compounds useful in the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive peptidomimetic is combined with a suitable carrier in order to facilitate effective administration of the composition. The compositions used in the present methods can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically acceptable carriers and diluents which are known to those skilled in the art. Examples of carriers or diluents for use with the subject peptidomimetics include, but are not limited to, water, saline, oils including mineral oil, ethanol, dimethyl sulfoxide, gelatin, cyclodextrans, magnesium stearate, dextrose, cellulose, sugars, calcium carbonate, glycerol, alumina, starch, and equivalent carriers and diluents, or mixtures of any of these. Formulations of the peptidomimetics of the invention can also comprise suspension agents, protectants, lubricants, buffers, preservatives, and stabilizers. To provide for the administration of such dosages for the desired therapeutic treatment, pharmaceutical compositions of the invention will advantageously comprise between about 0.1% and 45%, and especially, 1 and 15% by weight of the total of one or more of the peptidomimetics based on the weight of the total composition including carrier or diluent.

The peptidomimetics and compositions of the subject invention can also be administered utilizing liposome technology, slow release capsules, implantable pumps, and biodegradable containers. These delivery methods can, advantageously, provide a uniform dosage over an extended period of time.

The subject peptidomimetics can also be modified by the addition of chemical groups, such as PEG (polyethylene glycol). PEGylated peptides typically generate less of an immunogenic response and exhibit extended half-lives in vivo in comparison to peptides that are not PEGylated when administered in vivo. Methods for PEGylating proteins and peptides are known in the art (see, for example, U.S. Pat. No. 4,179, 337). The subject peptidomimetics can also be modified to improve cell membrane permeability. In one embodiment, cell membrane permeability can be improved by attaching a lipophilic moiety, such as a steroid, to the peptidomimetic. Other groups known in the art can be linked to peptidomimetics of the present invention.

The subject invention also concerns a packaged dosage formulation comprising in one or more containers at least one peptidomimetic of the subject invention formulated in a pharmaceutically acceptable dosage. The package can contain discrete quantities of the dosage formulation, such as tablet, capsules, lozenge, and powders. The quantity of peptidomimetic in a dosage formulation and that can be administered to a patient can vary from about 1 mg to about 2000 mg, more typically about 1 mg to about 500 mg, or about 5 mg to about 250 mg, or about 10 mg to about 100 mg.

Materials and Methods

Cells and reagents. Src-transformed NIH3T3/v-Src, NIH3T3/v-Src/pLucTKS3, NIH3T3/v-Src/pRLSRE, and Ras-transformed NIH3T3/v-Ras fibroblasts, human breast carcinoma MDA-MB-231, MDA-MB-435, MDA-MB-453 and MDA-MB-468 cells, as well as human lung carcinoma A459 cells have been previously described (Turkson et al. (2001); Yamauchi et al. (1993)). Cells were grown in Dulbecco's modified Eagle's medium (DMEM) containing 5% iron-supplemented bovine calf serum (BCS), with or without G418 or zeocin. The Apo-BrdU kit was from PharMingen (San Diego, Calif.).

Peptides. Peptides used in studies include PY*LKTK-AAVLLPVLLAAP (SEQ ID NO. 1) and PYLKTK-AAVLL-PVLLAAP (SEQ ID NO. 2) (the underlined amino acid sequence represents the membrane translocating sequence (MTS) (Rojas, M. et al. (1998))) and peptidomimetics based on PY*L and AY*L (where Y*=phosphotyrosine). Peptides were synthesized by the Peptide Synthesis Laboratory, Queen's University, Kingston, ON, Canada. Peptidomimetics were synthesized manually using standard Fmoc solid phase chemistry. Peptides or peptidomimetics were used at concentrations up to 1 mM as indicated.

Plasmids. The Stat3 reporter, pLucTKS3, driving expression of the firefly luciferase gene and the Stat3-independent plasmid, pRLSRE, containing two copies of the serum response element (SRE) from the c-fos promoter (Turkson, J. et al. (1998); Zhang, Y. et al. (2000)) that drives renilla luciferase gene (Promega; Madison, Wis.) expression, have been previously described (Turkson, J. et al. (2001); Turkson, J. et al. (1999)).

Recombinant baculoviruses and infection of Sf-9 insect cells. Stat1, Stat3, Jak1 and c-Src recombinant baculoviruses and infection of Sf-9 insect cells have been previously described (Zhang, Y. et al. (2000)). For protein expression of activated Stat1 or Stat3, Sf-9 insect cells were infected with viruses expressing either Stat1 or Stat3 in combination with viruses expressing Jak1 and/or c-Src.

Cytosolic extract preparation and luciferase assays. Cytosolic extract preparation from fibroblasts and luciferase assays were previously described (Turkson, J. et al. (1998); Turkson, J. et al. (1999)). Briefly, after two washes with PBS and equilibration for 5 min with 0.5 ml PBS-0.5 mM EDTA, cells were scraped off the dishes and the cell pellet was obtained by centrifugation (4,500×g, 2 min, 4° C.). Cells were resuspended in 0.4 ml of low-salt HEPES buffer (10 mM HEPES (pH 7.8), 10 mM KCl, 0.1 mM EGTA, 0.1 mM EDTA, 1 mM phenylmethylsulfonyl fluoride, and 1 mM dithiothreitol) for 15 min, lysed by the addition of 20 µl of 10% Nonidet P-40 (NP-40), and centrifuged (10,000×g, 30 s, 4° C.) to obtain the cytosolic supernatant, which was used for luciferase assays (Promega) measured with a luminometer. Cytosolic lysates containing activated Stat3 or Stat1 that were used for dissociation-reassociation analysis were prepared from baculovirus-infected Sf-9 insect cells as previously described (Turkson, J. et al. (2001); Zhang, Y. et al. (2000)). Briefly, cultured dishes of Sf-9 cells were washed twice with ice-cold 1×PBS and then PBS containing 1 mM sodium orthovanadate. Cells were then lysed in 1% NP-40 lysis buffer (50 mM HEPES (pH 7.9), 150 mM NaCl, 1% NP-40, mM NaF, 1 mM sodium orthovanadate, 1 mM tetrasodium pyrophosphate, 1 mM dithiothreitol, 0.5 mM phenylmethylsulfonyl fluoride, 2 mM EGTA, 2 mM EDTA, 0.1 µM aprotinin, 1 µM leupeptin, and 1 µM antipain) on ice for 10 min, and centrifuged (13,000×g, 30 s, 4° C.) to obtain lysate.

Nuclear extract preparation and gel shift assays. Nuclear extracts were prepared from cell lines and used for electrophoretic mobility shift assay (EMSA) as previously described (Garcia, R. et al. (1997); Yu, C. L. et al. (1995); Turkson, J. et al. (1998)). In some cases, cells were pre-treated with peptidomimetics for the indicated times (12-48 h) prior to harvesting for nuclear extract preparation. In other studies, nuclear extracts were pre-incubated with peptidomimetics for 30 min at room temperature prior to incubation with radiolabeled probe. The $^{32}$P-radiolabeled oligonucleotide probes used are hSIE (high affinity sis-inducible element, m67 variant, 5'-AGCTTCATTTCCCGTAAATCCCTA-3') (SEQ ID NO. 3) that binds both Stat1 and Stat3 (Garcia, R. et al. (1997); Wagner B. J. et al. (1990)) and MGFe (mammary gland factor element from the bovine β-casein gene promoter, 5'-AG-ATTTCTAGGAATTCAA-3') (SEQ ID NO. 4) that binds Stat1 and Stat5 (Gouilleux, F. et al. (1995); Seidel, H. M. et al. (1995)).

Dissociation-reassociation analysis. Two independent preparations of lysate (from baculovirus-infected Sf-9 cells) containing either active Stat1:Stat1 or Stat3:Stat3 were pooled together. Aliquots of mixed lysates of equal total protein were pre-treated with or without 30-300 μM PY*LKTK (SEQ ID NO. 5) or 3-1000 μM ISS 610 for 30 min prior to incubation with $^{32}$P-labeled hSIE and subjected to EMSA (Shuai, J. I et al. (1994)).

Cell proliferation, soft-agar growth and Apo-BrdU labeling studies. Proliferating fibroblasts and human tumor cells were counted by phase-contrast microscopy for viable cells (using tyrpan blue exclusion). Colony formation assays in six-well dishes and quantification of colonies by iodonitrotetrazolium violet have been previously described (Turkson, J. et al. (1999)). Treatment of cells with inhibitors was initiated 1 day after seeding cells by adding 75 μl of medium with or without inhibitor, and repeated every two to three days. Apoptosis was measured by Apo-BrdU labeling and following the supplier's (PharMingen; San Diego, Calif.) instructions. Cells (NIH3T3 or NIH3T3/v-Src) were first treated with or without PY*LKTK-MTS (SEQ ID NO. 1), or ISS 610 for 48 h prior to labeling and than analyzed by flow cytometry for detection of apoptotic cells.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Design of PY*L Peptidomimetics: Substitutions of Proline With Aromatic Groups Generate Strong Disruptors of Stat3 DNA-Binding Activity In Vitro It has been reported that PY*LKTK (SEQ ID NO. 5), the putative Stat3 SH2 domain-binding sequence, and the tripeptides PY*L and AY*L, disrupt Stat3:Stat3 dimer formation and subsequent Stat3 DNA-binding activity. Peptidomimetics of the invention can be prepared by replacing prolyl or alanyl residue at the peptide bond that is N-terminal to the phosphotyrosine (Y*) of a peptide such as PY*L or AY*L with an organic substituent such as an optionally substituted aryl or heteroaryl group. The activities of STATs were measured in nuclear extracts (prepared from epidermal growth factor (EGF)-stimulated fibroblasts) as DNA-bound protein complexes by electrophoretic mobility shift assay (EMSA). STAT-DNA complexes detected include Stat3:Stat3 homodimers (upper band), Stat1:Stat3 heterodimers (intermediate band) and Stat1:Stat1 homodimers (lower band) (FIG. 1A) when a $^{32}$P-labeled hSIE oligonucleotide probe is used, or Stat5:Stat5 (upper band) and Stat1:Stat1 dimers (lower band) (FIG. 1B) when $^{32}$P-labeled MGFe is used as a probe.

Figure 1B:
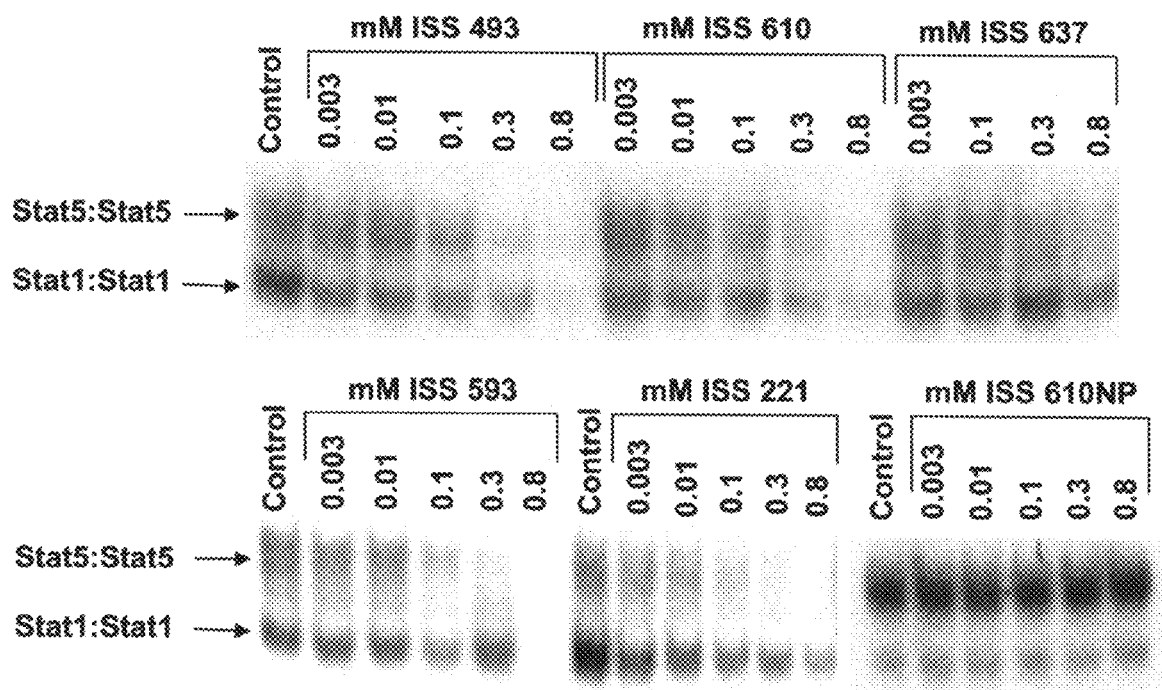

Pre-incubation of peptidomimetics of the invention with nuclear extracts results in potent and dose-dependent inhibition of DNA-binding activities of Stat3, and to a lesser extent of Stat1 or Stat5 (FIGS. 1A and 1B). From densitometric analysis of band intensities, the $IC_{50}$ values (concentration of peptidomimetic at which DNA-binding activity is reduced by 50%), which are reported in Table 3, were determined. Peptidomimetics ISS 610 and ISS 637 exhibited a 5-fold increase in potency (compared to tripeptides PY*L or AY*L) in inhibiting Stat3 DNA-binding activity in vitro ($IC_{50}$ value decreased from 217±55 μM (AY*L) or 182±15 μM (PY*L) to 42±23 μM (ISS 610) or 55±35 μM (ISS 637)) (Table 3 and FIG. 1A). In their inhibitory activities, these peptidomimetics also show preference for Stat3 over Stat1 or Stat5. The non-tyrosine-phosphorylated form of ISS 610 (ISS 610NP) has no effect on Stat3 (and Stat1 or Stat5) DNA-binding activity in vitro (FIGS. 1A and 1B, bottom panels), reflecting the importance of the pTyr for disruption of Stat3 by peptidomimetics of the invention. These findings provide support for the engagement of pTyr-SH2 interaction as being the basis for Stat3 dimer disruption by peptidomimetics of the invention, such as ISS 610 (see below).

Peptidomimetics ISS 493, ISS 610, and ISS 637 exhibited preferential suppression of Stat3 activity over those of Stat1 or Stat5 (Table 4), while others, such as in ISS 593, have enhanced potency against Stat5 over Stat3 ($IC_{50}$ values of 10±6 μM). The inhibition of Stat5 has important implications for some types of human tumors, such as chronic myelogenous leukemia, which depend on constitutively-active Stat5 for growth and survival (Bowman, T. et al. (2000); Smithgall, T. E. et al. (2000); Lin, J. et al. (2000)).

EXAMPLE 2

Disruption of STAT Dimerization: Evidence for Dissociation of STAT Dimers

A STAT dimerization disruption model (Turkson, J. et al. (2001)) has been proposed to define the interaction of Stat3:Stat3 dimers with PY*LKTK (SEQ ID NO. 5), PY*L, and AY*L. In this model, phosphopeptides engage in pTyr-SH2 interactions with STAT:STAT dimers, which results in STAT dimer dissociation into monomers (in complexes with phosphopeptides), some of which may in turn reassociate into STAT dimers. Using this model, dissociation-reassociation analysis (Shuai, K. et al. (1994)) was performed with two independent cell lysate preparations, one containing only active Stat1:Stat1 dimers and the other only Stat3:Stat3 dimers. Lysates were mixed together with or without PY*LKTK (SEQ ID NO. 5) or peptidomimetic ISS 610 or its non-phosphorylated counterpart, ISS 610NP, and then incubated with radiolabeled hSIE probe (SEQ ID NO. 3) and subjected to EMSA analysis.

Figure 2A:
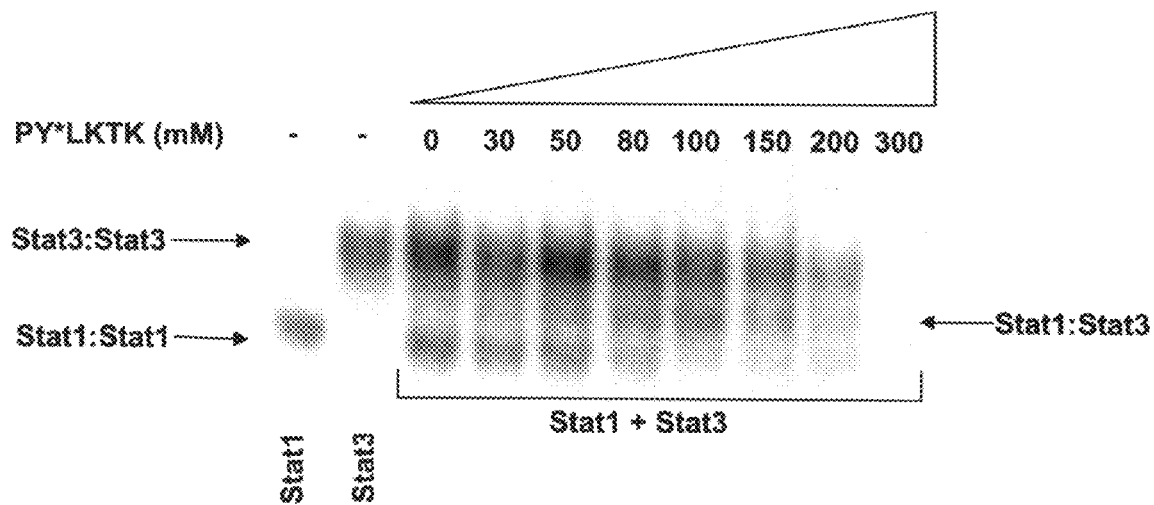
FIGS. 2A and 2B show evidence for dissociation of STAT dimers by phosphopeptide or peptidomimetic. Cell lysates contain either only activated Stat1 (lane 1), Stat3 (lane 2) or both (pooled lysates, shown in lanes 3-10) and are treated (lanes 4-10) with the indicated concentrations of PY*LKTK (SEQ ID NO. 5) (FIG. 2A) or ISS 610 (FIG. 2B) for 30 min at room temperature prior to incubation with radiolabeled hSIE oligonucleotide probe (SEQ ID NO. 3). Positions of STAT:DNA complexes in gel are labeled. Cell lysates were prepared from recombinant baculovirus-infected Sf-9 cells as described in the Materials and Methods section.
Figure 2B:
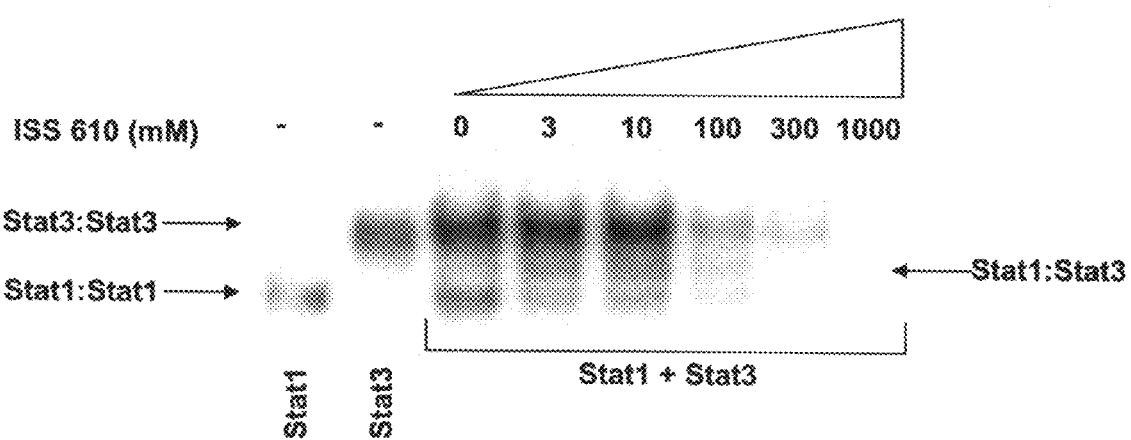

Either cell lysate preparation alone shows one band corresponding to Stat1:Stat1 dimers (FIGS. 2A and 2B, lane 1) or Stat3:Stat3 dimers (FIGS. 2A and 2B, lane 2). For mixed cell lysates, two bands with migrations consistent with Stat1:Stat1 dimers (lower band) or Stat3:Stat3 dimers (upper band) (FIGS. 2A and 2B, lane 3) are observed in the absence of the phosphopeptide, PY*LKTK (SEQ ID NO. 5), or ISS 610. However, EMSA analysis of mixed cell lysates that are pre-incubated with PY*LKTK (SEQ ID NO. 5) or ISS 610 shows three bands: i) lower and upper bands corresponding to Stat1:Stat1 and Stat3:Stat3 dimers, respectively (FIGS. 2A and 2B, lanes 4 to 8), which are of decreasing intensities with increasing concentrations of phosphopeptide or peptidomimetic, consistent with results in FIG. 1A; and ii) appearance of an additional intermediate band representing Stat1:Stat3 heterodimers (FIGS. 2A and 2B, lanes 4 to 7) (Shuai, K. et al. (1994)) that hitherto were not present and could only have formed from random reassociation of two dissociated phosphorylated monomers. Results also show decreasing band intensities or complete disappearance of the three STAT-DNA complexes at higher concentrations of PY*LKTK (SEQ ID NO. 5) or ISS 610 (FIG. 2A, lane 10, and FIG. 2B, lane 8) due primarily to total disruption of all STAT:STAT dimers and formation of only complexes of STAT protein with peptidomimetics (or phosphopeptides). The apparently stronger disruption of Stat1:Stat1 dimer might be due to a relatively lower amount of Stat1 protein in starting material (lysate) compared to Stat3 protein. The non-phosphorylated ISS 610NP has no effect (data not shown), which demonstrates the importance of pTyr in peptidomimetics of the invention for disruption of Stat3 dimers.

EXAMPLE 3

Figure 3A:
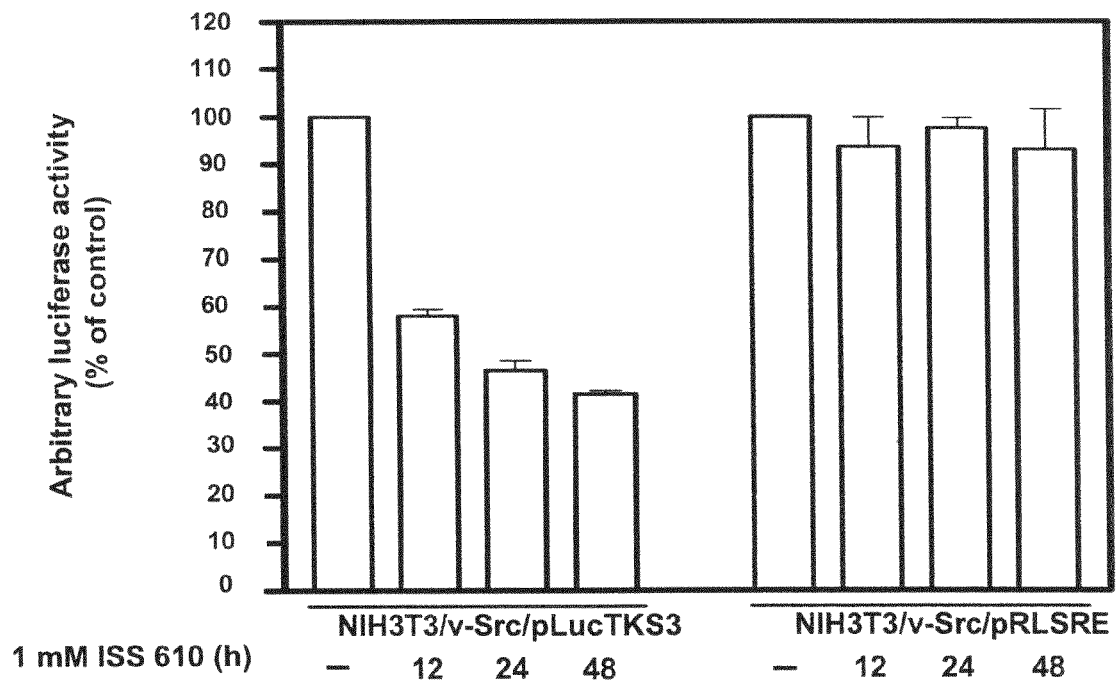
FIGS. 3A-3F show evaluation of peptidomimetic effects on Stat3 activation and Stat3-mediated gene expression in intact cells, and on Src-transformation.
Figure 3B:
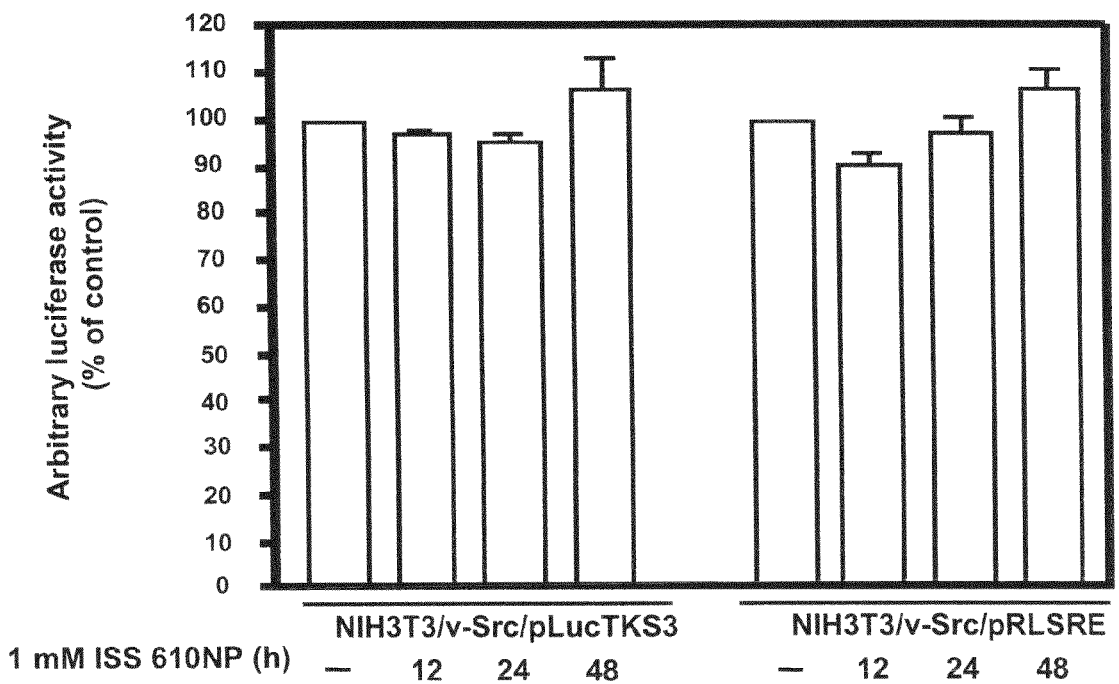
Figure 3C:
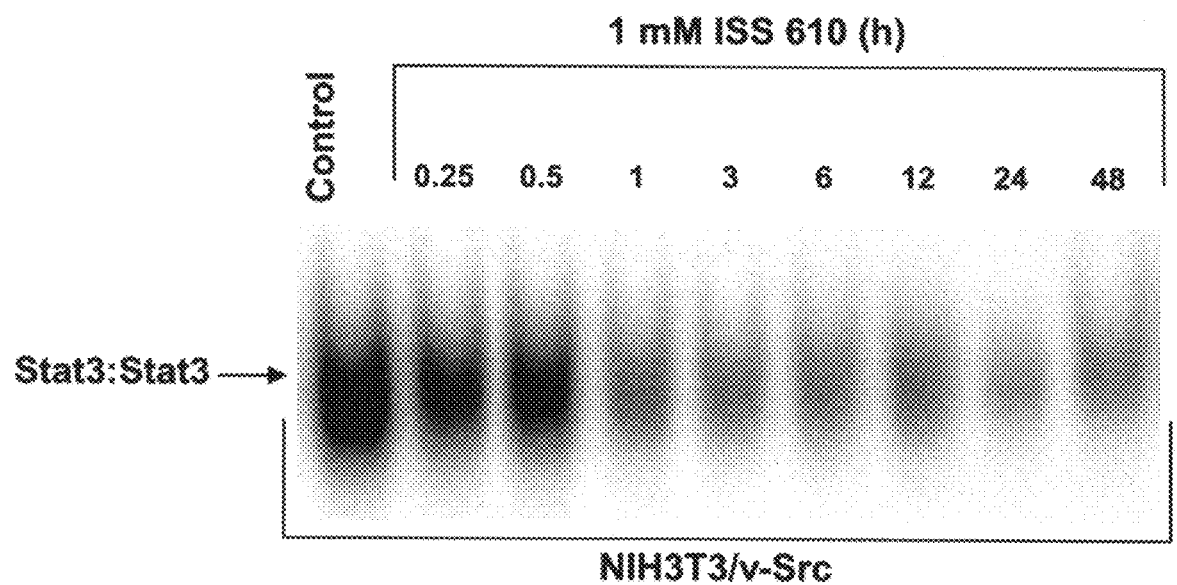
Figure 3D:
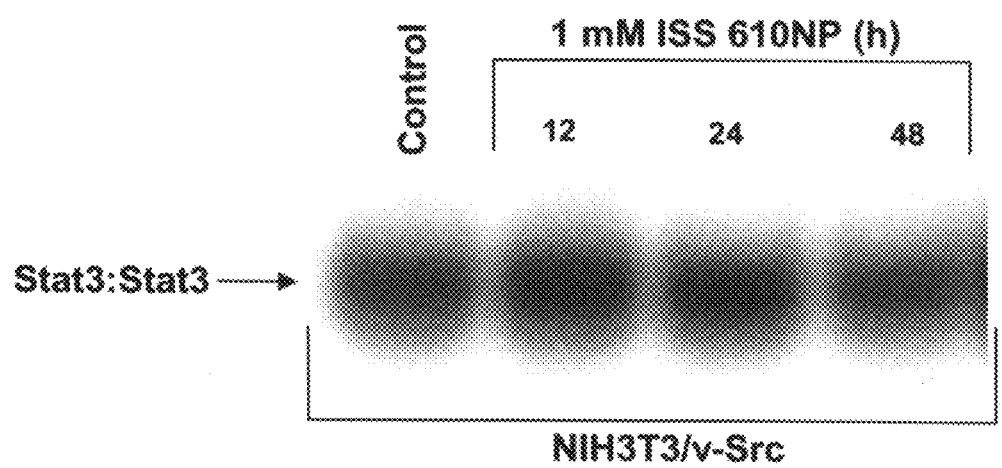
Figure 3E:
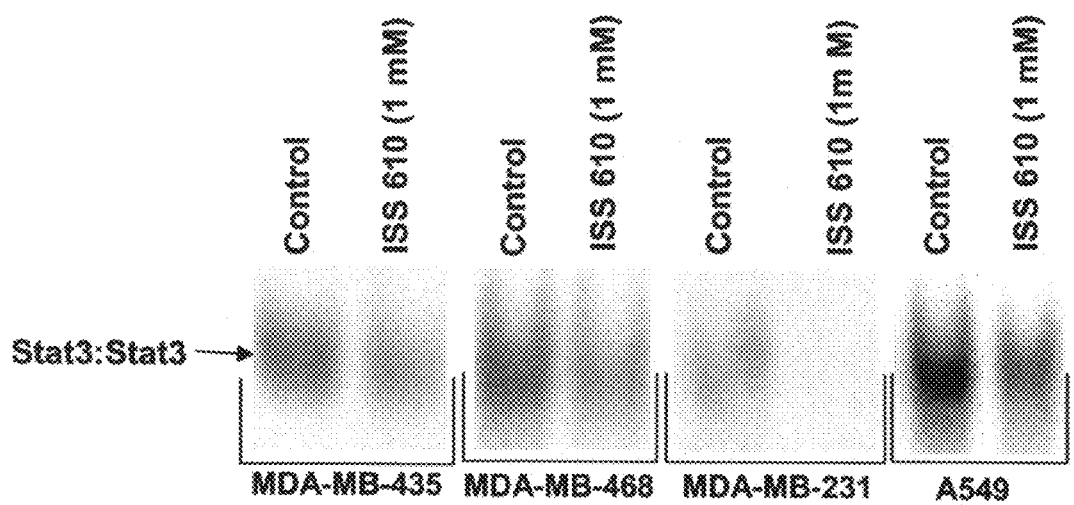

Peptidomimetic Selectively Blocks Stat3 Signaling and Constitutively-Active STAT3-Dependent V-SRC Transformation PY*LKTK-MTS (SEQ ID NO. 1) (MTS, membrane translocation sequence, is a sequence of hydrophobic amino acids that facilitates transport of peptides across cell membranes) (Rojas, M. et al. (1998)) inhibits constitutive Stat3 activation in Src-transformed fibroblasts (Turkson J. et al. (2001)). Peptidomimetics which are phosphorylated on tyrosine have reduced membrane-permeability, particularly if they do not contain MTS to enhance permeability. Thus, peptidomimetic ISS 610 was used at 1 mM concentrations in whole-cell studies. Luciferase reporter assays on Src-transformed mouse-cells that stably express Stat3-dependent and Stat3-independent dual luciferase reporters (Turkson J. et al. (2001)), and are treated with ISS 610 show a significant suppression of transcriptional induction of the Stat3-dependent luciferase reporter, pLucTKS3, with no effect on the induction of the Stat3-independent luciferase reporter, pRLSRE (FIG. 3A). Similarly, DNA-binding studies and EMSA analysis reveal a time-dependent reduction of Stat3 activation in Src-transformed fibroblasts (FIG. 3C), human non-small cell lung carcinoma, (A549) and breast carcinomas (MDA-MB-231, MDA-MB-435, and MDA-MB-468) cells that harbor constitutive Stat3 activation (Garcia R. et al. (2001); Song, L. et al. (2003)) and are treated with ISS 610 (FIG. 3E, second lane for each cell line). Inhibition of Stat3-dependent luciferase induction and Stat3 activation in whole cells was not complete at 48 h post-treatment (FIGS. 3A and 3C), possibly due to low intracellular levels of peptidomimetic as a result of weak uptake, rapid degradation, or both. In other studies, the effect of ISS 610 on ligand (EGF)-induced STAT activation in mouse fibroblasts was evaluated and preferential inhibition of activation of Stat3, and to a lesser extent of that of Stat1 was observed (data not shown). Moreover, the non-phosphorylated ISS 610NP has no effect on Stat3 activation in Src-transformed cells or Stat3-mediated gene expression (FIGS. 3B and 3D), indicating that pTyr is required for disruption of interaction between Stat3 dimers. Thus, peptidomimetics of the invention can selectively suppress constitutive Stat3 signaling in whole cells.

Figure 3F:
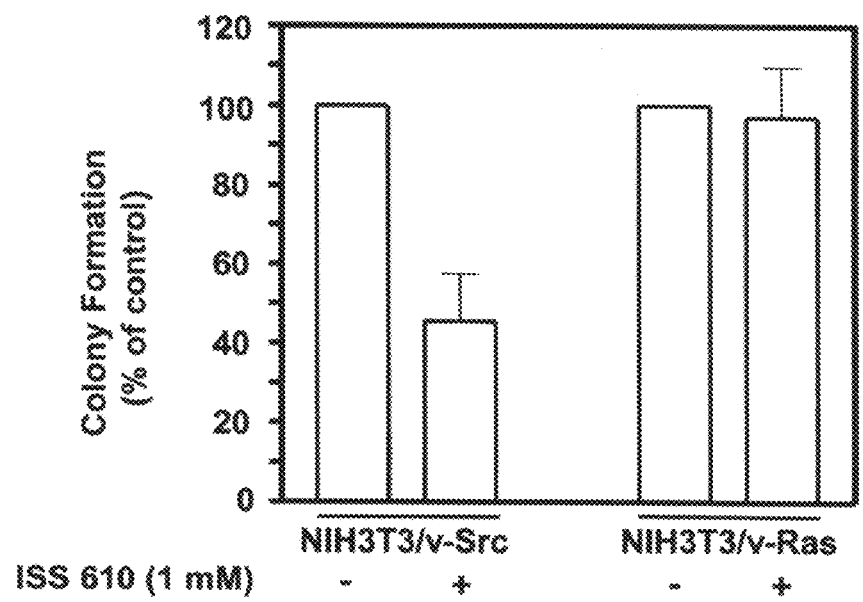

Previous studies with PY*LKTK-MTS (SEQ ID NO. 1) (Turkson, J. et al., 2001)) confirmed that inhibition of constitutive Stat3 activation blocks Src transformation (Turkson, J. et al. (1998); Turkson, J. et al., (1999); Bromberg, J. R. et al. (1998)). Using growth in soft agar as a measure of transformation, the effect of representative peptidomimetic ISS 610 was determined. Growth of NIH3T3/v-Src in soft-agar suspension is significantly suppressed by the addition of ISS 610 (FIG. 3F). In contrast, ISS 610 has no effect on soft-agar growth of Stat3-independent Ras-transformed fibroblasts (NIH3T3/v-Ras) (FIG. 3F). These findings indicate that selective blocking of constitutive Stat3 signaling by the peptidomimetic inhibitor ISS 610 suppresses transformation of mouse fibroblasts by v-Src.

EXAMPLE 4

Figure 4A:
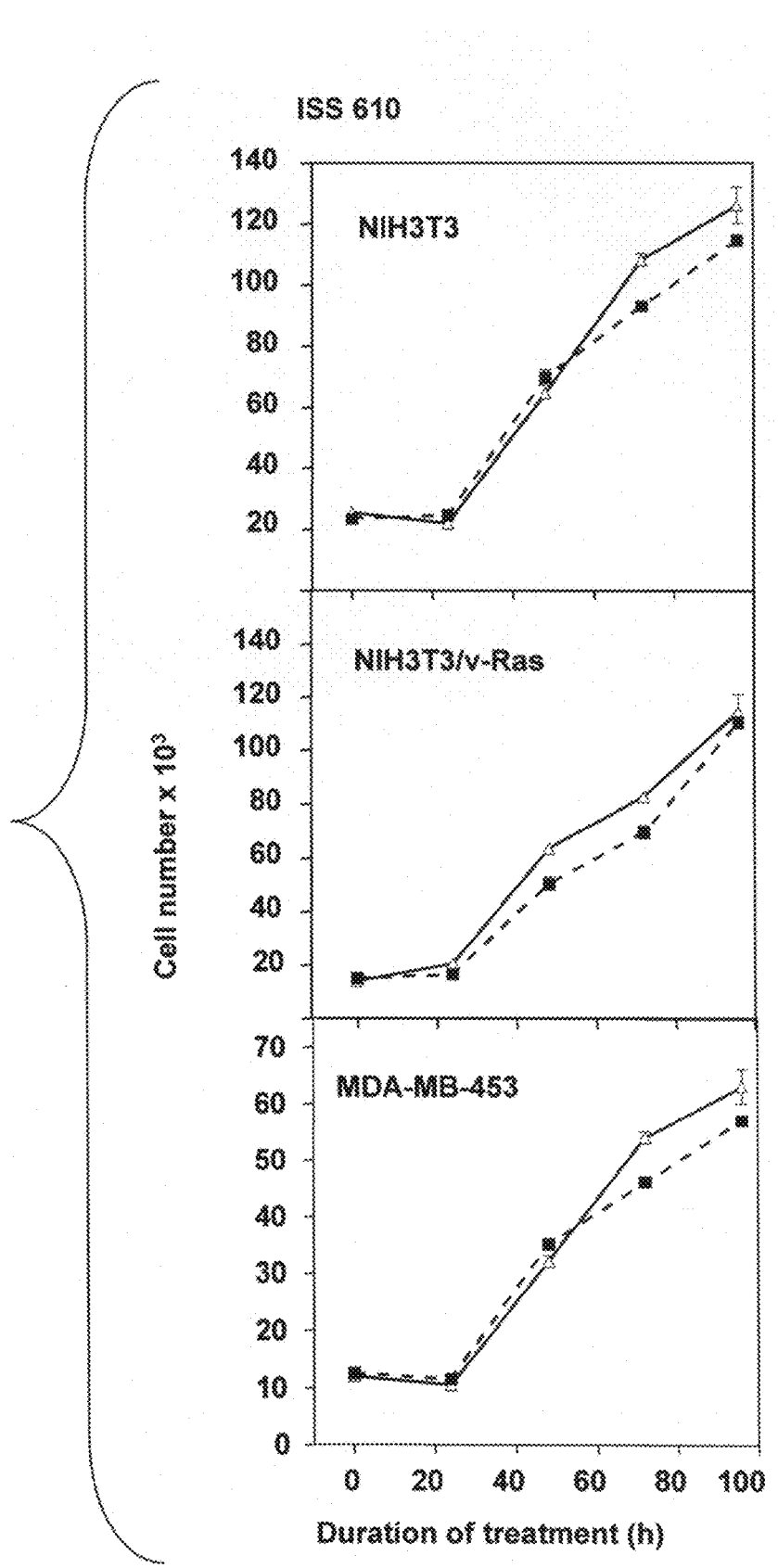
FIGS. 4A-C show evaluation of peptidomimetic effects on cell proliferation. Growth curves for transformed and tumor cells. Normal and transformed fibroblasts (NIH3T3, NIH3T3/v-Src, or NIH3T3/v-Ras) as well as human breast carcinoma (MDA-MB-231, MDA-MB-435, or MDA-MB-453) cells were treated with or without compounds and counted by trypan blue exclusion on each of four days. Cells were untreated (dotted lines) or treated with 1 mM ISS 610 or PY*LKTK-MTS (SEQ ID NO. 1) (solid lines). Values are the mean and S.D. of four independent determinations.
Figure 4B:
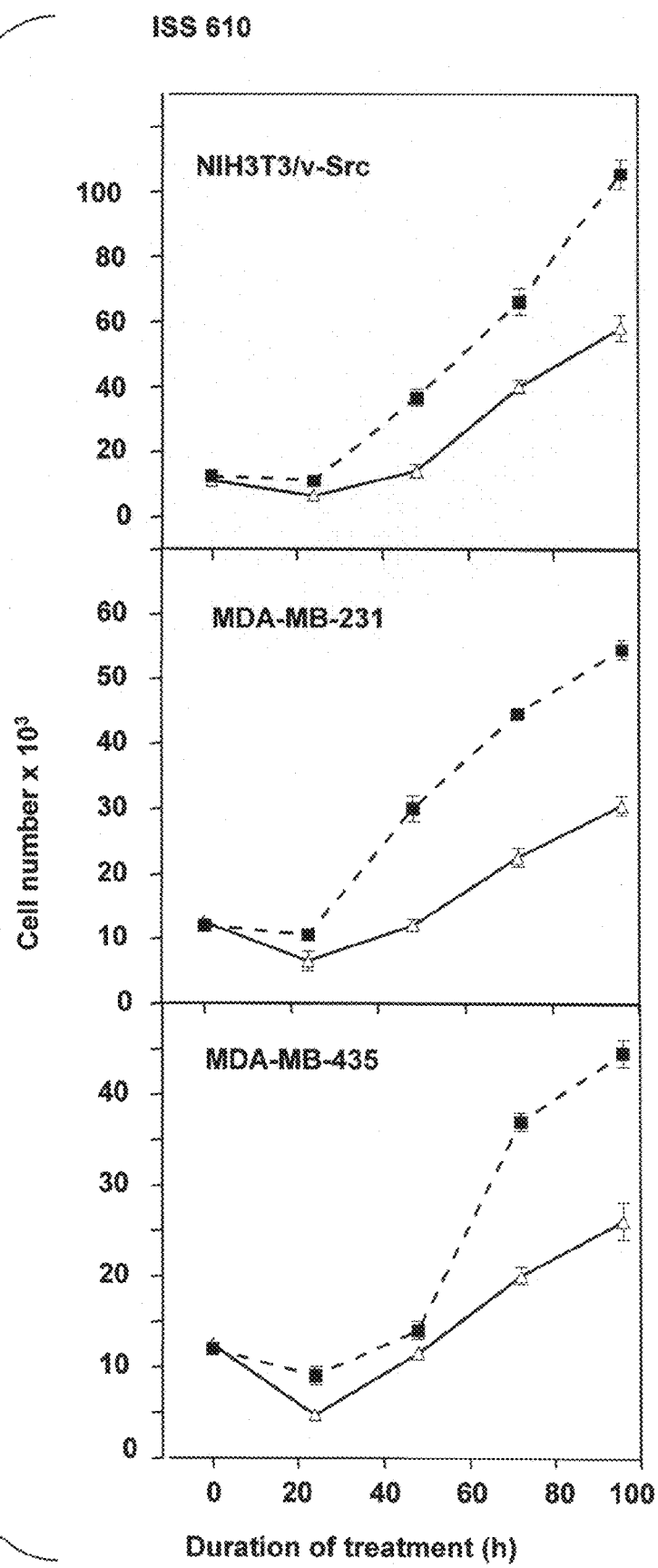
Figure 4C:
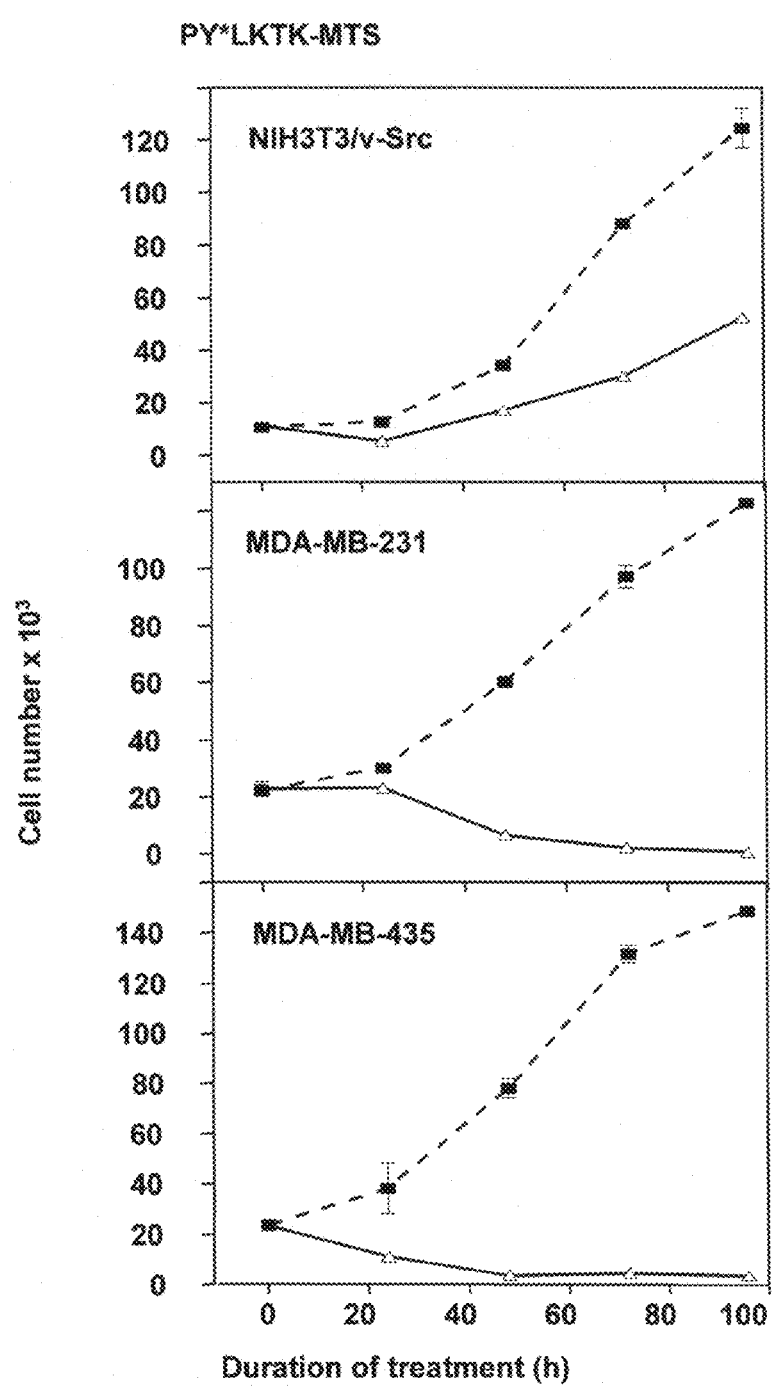

ISS 610 Induces Growth Inhibition of Malignant Cells that Contain Persistent Stat3 Activity Stat3 has an essential role in cell proliferation, and constitutively-active Stat3 is required for growth of transformed and tumor cells that harbor aberrant Stat3 signaling. Studies were performed to determine the effects of the peptidomimetic-mediated inhibition of Stat3 on cell proliferation using trypan blue exclusion for viable cell counts. Results show that treatment with ISS 610 (or PY*LKTK-MTS for comparison) (SEQ ID NO. 1) of Src-transformed mouse fibroblasts (NIH3T3/v-Src), or the human breast carcinoma cells MDA-MB-231 and MDA-MB-435 that harbor constitutively-active Stat3 significantly suppresses proliferation compared to control (non-treated cells) (FIGS. 4B and 4C). In comparison to the effect observed for PY*LKTK-MTS (SEQ ID NO. 1), the inhibition of cell proliferation by ISS 610 was only partial. Unlike the phosphopeptide, which is linked at the C-terminus to the membrane-translocation sequence (MTS) (Rojas, M. et al. (1998)) to facilitate intracellular uptake across cell membrane, ISS 610 lacks this MTS and, therefore, may not be efficiently taken up into cells, which will in turn be reflected in its biological activity. Treatment of cells that lack constitutive Stat3 activity (e.g., normal NIH3T3 cells, Ras-transformed counterparts (NIH3T3/v-Ras), or MDA-MB-453 cells) shows no effect on cell proliferation (FIG. 4A, data not shown). Thus, ISS 610 does not appear to have any general cytostatic or cytotoxic effects. These findings show that peptidomimetics of the invention inhibit growth of transformed mouse and human tumor cells that harbor constitutive Stat3 activity.

EXAMPLE 5

Peptidomimetics Induces Apoptosis in Transformed Fibroblasts that Exhibit Persistent Stat3 Activity Because one of the functions of Stat3 is to protect transformed or tumor cells from apoptosis (Catlett-Falcone, R. et al. (1999b); Epling-Burnette, P. K. et al. (2001); Grandis, J. R. et al. (2000); Bowman, T. et al. (2000b); Bromberg, J. F. et al. (1999)), the ability of peptidomimetics of the invention (and PY*LKTK-MTS for comparison) (SEQ ID NO. 1) to induce apoptosis in Stat3-dependent transformed fibroblasts was evaluated. Viral Src-transformed NIH3T3/v-Src fibroblasts were treated with or without compounds for 48 h. Treated cells were then labeled with Apo-BrdU (PharMingen; San Diego, Calif.) for detection of DNA breaks. Results from flow cytometric analysis of cells show dramatic increases in incorporated BrdUTP in Src-transformed fibroblasts treated with PY*LKTK-MTS (SEQ ID NO. 1) or ISS 610 compared to controls (non-treated cells or treated with control peptide, PYLKTK-MTS (SEQ ID NO. 2)) or to normal NIH3T3 fibroblasts treated with peptides or peptidomimetic (Table 5). Together, these findings show that PY*LKTK (SEQ ID NO.

5) and ISS 610 induce apoptosis in Stat3-dependent transformed cells but not in normal cells. This observation reflects the inhibition of Stat3 activity and its biological function, which together with the other data demonstrates that selective suppression of constitutive Stat3 activation and its biological function induces apoptosis in model transformed cells that harbor constitutive Stat3 activity.

TABLE 3

Disruption of Stat3 DNA-binding activity by peptidomimetics having the structure shown in formula I and R group shown. Nuclear extracts containing active Stat3 were pre-incubated for 30 min with or without peptidomimetics prior to incubation with radiolabeled hSIE probe and analysis by EMSA.

| Compound or Compound Designation | R | IC$_{50}$ (μM)** |
|---|---|---|
| Prolylphosphotyrosylleucine | pyrrolidinyl | 182 +/− 15 |
| Alanylphosphotyrosylleucine | H$_3$C–CH– (methyl ethyl) | 217 +/− 55 |
| ISS 248 | 3-aminophenyl | ne |
| ISS 265 | 2-aminophenyl | ne |
| ISS 375 | 4-nitro-2-fluorophenyl (O$_2$N, F substituted) | ne |
| ISS 610 | 4-cyanophenyl (NC-phenyl) | 42 +/− 23 |
| ISS 637 | 2,6-dimethoxyphenyl (OCH$_3$, OCH$_3$) | 55 +/− 35 |
| ISS 219 | 3-pyridyl | 232 +/− 16 |
| ISS 221 | 2-methyl-3-pyridyl (CH$_3$) | 75 +/− 36 |
| ISS 593 | 2,6-dichloro-3-fluoro-pyridyl (F, Cl, Cl) | 48 +/− 32 |
| ISS 223 | 6-methyl-3-pyridyl (H$_3$C–pyridyl) | 225 +/− 15 |
| ISS 249 | 6-amino-3-pyridyl (H$_2$N–pyridyl) | ne |
| ISS 493 | 5-methylpyrazinyl (H$_3$C–pyrazinyl) | 38 +/− 16 |
| ISS 352 | 1-naphthyl | 410 +/− 15 |
| ISS 353 | 2-naphthyl | 650 +/− 22 |
| ISS 355 | 4-biphenyl | ne |
| ISS 360 | 2-biphenyl | 420 +/− 35 |
| ISS 363 | 3-quinolinyl | 643 +/− 43 |
| ISS230 | H$_3$C– | ne |
| ISS231 | H$_3$C–CH$_2$–CH$_2$– (propyl) | ne |
| ISS234 | (H$_3$C)$_2$CH– (isopropyl) | ne |

TABLE 3-continued

Disruption of Stat3 DNA-binding activity by peptidomimetics having the structure shown in formula I and R group shown. Nuclear extracts containing active Stat3 were pre-incubated for 30 min with or without peptidomimetics prior to incubation with radiolabeled hSIE probe and analysis by EMSA.

| Compound or Compound Designation | R | $IC_{50}$ (μM)** |
|---|---|---|
| ISS227 | 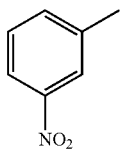 | 245 +/− 6 |

**Values are the means and standard deviations of at least 3 independent assays. $IC_{50}$, concentration of peptidomimetic at which DNA-binding is reduced by 50%; ne, no effect at 1 mM. Results are representative peptidomimetics from over 80 that have been evaluated.

TABLE 4

Selective disruption of STAT family members by peptidometics Nuclear extracts containing active Stat1, Stat3 and Stat5 were pre-incubated with or without peptidomimetics for 30 min prior to incubation with radiolabeled hSIE probe (SEQ ID NO. 3) and EMSA analysis.
$IC_{50}$ values (μM) against STAT Dimers**

| Peptido-mimetic | Stat3:Stat3 | Stat1:Stat3 | Stat1:Stat1 | Stat5:Stat5 |
|---|---|---|---|---|
| ISS 221 | 75 +/− 36 | 455 +/− 97 | 310 +/− 74 | 50 +/− 12 |
| ISS 493 | 38 +/− 16 | 230 +/− 22 | 273 +/− 22 | 300 +/− 22 |
| ISS 593 | 48 +/− 32 | 87 +/− 15 | 175 +/− 65 | 10 +/− 6 |
| ISS 610 | 42 +/− 23 | 125 +/− 15 | 310 +/− 145 | 285 +/− 32 |
| ISS 637 | 55 +/− 35 | 195 +/− 12 | 255 +/− 55 | 695 +/− 123 |

**Values are the means and standard deviations of at least 3 independent assays. $IC_{50}$, concentration of peptidomimetic at which DNA-binding is reduced by 50%; ne, no effect at 1 mM. Results are representative peptidomimetics from over 80 that have been evaluated.

TABLE 5

Flow cytometric analysis for percent of apoptotic cells treated with PY*LKTK-MTS (SEQ ID NO. 1) and ISS 610.

| | NIH3T3 | NIH3T3/v-Src |
|---|---|---|
| Control | 2.1% | 1.8% |
| 1 mM PYLKTK-MTS (SEQ ID NO. 2) | 1.2% | 0.4% |
| 1 mM PY*LKTK-MTS (SEQ ID NO. 1) | 3.7% | 27.6% |
| 1 mM ISS 610 | 0.3% | 21.4% |

Cells were treated with compounds for 48 h, labeled with Apo-BrdU and analyzed by flow cytometry for percent apoptotic cells. Control represents no treatment.

It should be understood that the examples and embodiments described herein are for illustrative purposes only and that various modifications or changes in light thereof will be suggested to persons skilled in the art and are to be included within the spirit and purview of this application.

REFERENCES

U.S. Pat. No. 4,179,337

Akira, S. (2000) "Roles of STAT3 defined by tissue-specific gene targeting" *Oncogene* 19: 2607-2611.

Becker, S. et al. (1998) "Three-dimensional structure of the Stat3beta homodimer bound to DNA" *Nature* 394:145-151.

Berg, T. et al. (2002) "Small-molecule antagonists of Myc/Max dimerization inhibit Myc-induced transformation of chicken embryo fibroblasts" *Proc. Natl. Acad. Sci. U.S.A.* 99:3830-3835.

Bowman, T. et al. (2000a) "STATs in oncogenesis" *Oncogene* 19:2474-2488.

Bowman, T. et al. (2000b) "Stat3-mediated Myc expression is required for Src oncogenesis and PDGF-induced mitogenesis" *Proc. Natl. Acad. Sci. U.S.A.* 98:7319-7324.

Bromberg, J. F. et al. (1998) "Stat3 activation is required for cellular transformation by v-src" *Mol. Cell. Biol.* 18:2553-2558.

Bromberg, J. F. et al. (1999) "Stat3 as an oncogene" *Cell* 98:295-303.

Bromberg, J. and Darnell, J. E., Jr. (2000) "The role of STATs in transcriptional control and their impact on cellular function" *Oncogene* 19:2468-2473.

Buettner, R. et al. (2002) "Activated STAT signaling in human tumors provides novel molecular targets for therapeutic intervention" *Clin. Cancer Res.* 8:945-954.

Catlett-Falcone, R. et al. (1999a) "STAT proteins as novel targets for cancer therapy. Signal transducer an activator of transcription" *Curr. Opin. Oncol.* 11:490-496.

Catlett-Falcone, R. et al. (1999b) "Constitutive activation of Stat3 signaling confers resistance to apoptosis in human U266 myeloma cells" *Immunity* 10:105-115.

Chen, X. et al. (1998) "Crystal structure of a tyrosine phosphorylated STAT-1 dimer bound to DNA" *Cell* 93:827-839.

Darnell, J. E., Jr. (1997) "STATs and gene regulation" *Science* 277:1630-1635.

Darnell, J. E., Jr. (2002) "Transcription factors as targets for cancer therapy" *Nat. Rev. Cancer* 2:740-749.

Epling-Burnette, P. K. et al. (2001) "Inhibition of STAT3 signaling leads to apoptosis of leukemic large granular lymphocytes and decreased Mcl-1 expression" *J. Clin. Invest.* 107:351-362.

Frank, D. A. (1999) "STAT signaling in the pathogenesis and treatment of cancer" *Mol. Med.* 5:432-456.

Garcia, R. et al. (1997) "Constitutive activation of Stat3 in fibroblasts transformed by diverse oncoproteins and in breast carcinoma cells" *Cell Growth Diff.* 8:1267-1276.

Garcia, R. and Jove, R. (1998) "Activation of STAT transcription factors in oncogenic tyrosine kinase signaling" *J. Biomed. Sci.* 5:79-85.

Garcia, R. et al. (2001) "Constitutive activation of Stat3 by the Src and JAK tyrosine kinases participates in growth regulation of human breast carcinoma cells" *Oncogene* 20:2499-2513.

Gouilleux, F. et al. (1995) "Prolactin and interleukin-2 receptors in T lymphocytes signal through a MGF-STAT5-like transcription factor" *Endocrinology* 136:5700-5708.

Grandis, J. R. et al. (2000) "Constitutive activation of Stat3 signaling abrogates apoptosis in squamous cell carcinogenesis in vivo" *Proc. Natl. Acad. Sci. U.S.A.* 97:4227-4232.

Hirano, T., et al. (2000) "Roles of STAT3 in mediating the cell growth, differentiation and survival signals relayed through the IL-6 family of cytokine receptors" *Oncogene* 19:2548-2556.

Horvath, C. M. (2000) "STAT proteins and transcriptional responses to extracellular signals" *Trends Biochem. Sci.* 25:496-502.

Johnson, P. J. et al. (1985) "Overexpressed pp 60c-src can induce focus formation without complete transformation of NIH 3T3 cells" *Mol. Cell. Biol.* 5:1073-1083.

Jones, G. et al. (1997) "Development and validation of a genetic algorithm for flexible docking" *J. Mol. Biol.* 267: 727-748.

Kotenko, S. V. and Pestka, S. (2000) "Jak-Stat signal transduction pathway through the eyes of cytokine class II receptor complexes" *Oncogene* 19:2557-2565.

Lin, T. S. et al. (2000) "STAT signaling in the pathogenesis and treatment of leukemias" *Oncogene* 19:2496-2504.

Lin, J. and Leonard, W. J. (2000) "The role of Stat5a and Stat5b in signaling by IL-2 family cytokines" *Oncogene* 19:2566-2576.

Merrifield, R. B. (1963) "Solid Phase Peptide Synthesis. I. The Synthesis of a Tetrapeptide" *J. Amer. Chem. Soc.* 85:2149-2154.

Rojas, M. et al. (1998) "Genetic engineering of proteins with cell membrane permeability" *Nature Biotechnology* 16:370-375.

Sasse, J. et al. (1997) "Mutational analysis of acute-phase response factor/Stat3 activation and dimerization" *Mol. Cell. Biol.* 17:4677-4686.

Schindler, C. and Darnell, J. E., Jr. (1995) "Transcriptional responses to polypeptide ligands: the JAK-STAT pathway" *Annu. Rev. Biochem.* 64:621-651.

Seidel, H. M. et al. (1995) "Spacing of palindromic half sites as a determinant of selective STAT (signal transducers and activators of transcription) DNA binding and transcriptional activity" *Proc. Natl. Acad. Sci. U.S.A.* 92:3041-3045.

Seidel, H. et al. (2000) "Pharmacological intervention in the JAK/STAT signaling pathway" *Oncogene* 19:2645-2656.

Shuai, K. et al. (1993) "A single phosphotyrosine residue of Stat91 required for gene activation by interferon-gamma" *Science* 261:1744-1746.

Shuai, K. et al. (1994) "Interferon activation of the transcription factor Stat91 involves dimerization through SH2-phosphotyrosyl peptide interactions" *Cell* 76:821-828.

Song, J. I. and Grandis, J. R. (2000) "STAT signaling in head and neck cancer" *Oncogene* 19:2489-2495.

Stark, G. R. et al. (1998) "How cells respond to interferons" *Annu. Rev. Biochem.* 67:227-264.

Smithgall, T. E. et al. (2000) "Control of myeloid differentiation and survival by stats" *Oncogene* 19:2612-2618.

Turkson, J. et al. (1998) "Stat3 activation by Src induces specific gene regulation and is required for cell transformation" *Mol. Cell. Biol.* 18:2545-2552.

Turkson, J. et al. (1999) "Requirement for Ras/Rac1-Mediated p38 and c-Jun N-Terminal Kinase Signaling in Stat3 Transcriptional Activity Induced by the Src Oncoprotein" *Mol. Cell. Biol.* 19:7519-7528.

Turkson, J. and Jove, R. (2000) "STAT proteins: novel molecular targets for cancer drug discovery" *Oncogene* 19:6613-6626.

Turkson, J. et al. (2001) "Phosphotyrosyl peptides block Stat3-mediated DNA-binding activity, gene regulation and cell transformation" *J. Biol. Chem.* 276:45443-45455.

Wagner, B. J. et al. (1990) "The SIF binding element confers sis/PDGF inducibility onto the c-fos promoter" *EMBO J.* 9:4477-4484.

Xi, L. et al. (2002) "Activation of Stat3 by Receptor Tyrosine Kinases Regulates Survival in Human Non-Small Cell Carcinoma Cells" *Oncogene* (in press).

Yamauchi, K. et al. (1993) "Phosphatidylinositol 3-kinase functions upstream of Ras and Raf in mediating insulin stimulation of c-fos transcription" *J. Biol. Chem.* 268: 14597-14600.

Yu, C. L. et al. (1995) "Enhanced DNA-binding activity of a Stat3-related protein in cells transformed by the Src oncoprotein" *Science* 269:81-83.

Zhang, Y. et al. (2000) "Activation of Stat3 in v-Src Transformed Fibroblasts Requires Cooperation of Jak1 Kinase Activity" *J. Biol. Chem.* 275:24935-24944.

We claim:

1. A method for inhibiting growth or replication, or inducing apoptosis in a target cell having aberrant or constitutive expression of Stat3, said method comprising contacting the target cell with a composition comprising a peptidomimetic having the structure shown in formula I:

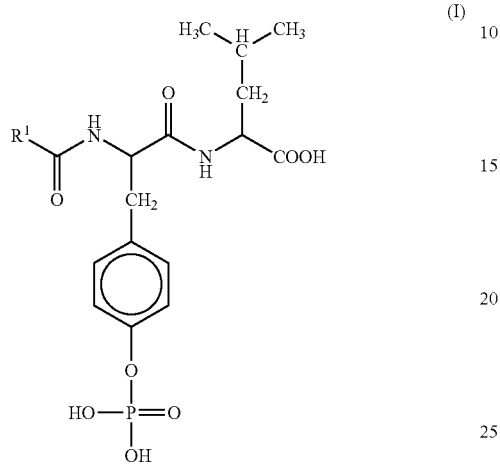
(I)

wherein
R$^1$ is selected from the group consisting of alkoxy, cycloalkyl, cycloalkoxy, aryl, aryloxy, alkylcarbonyl, alkoxycarbonyl, cycloalkylcarbonyl, heteroalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO$_2$, —NH$_2$, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, and heterocycloalkoxycarbonyl;

or a salt thereof.

2. The method according to claim 1, wherein said peptidomimetic is selected from the group consisting of:

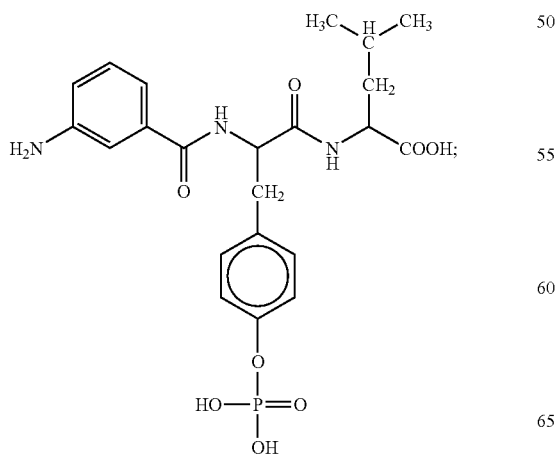

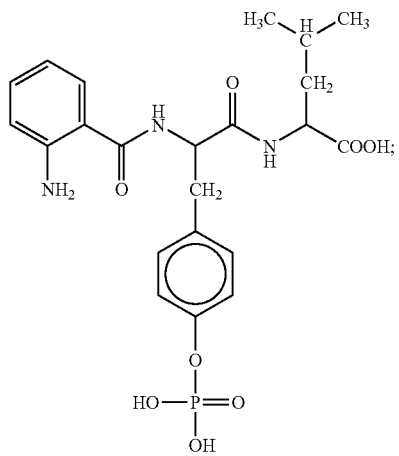

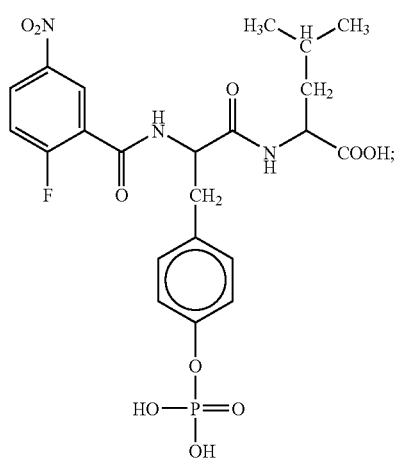

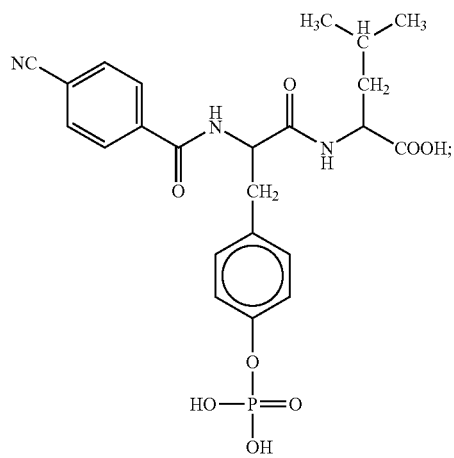

-continued
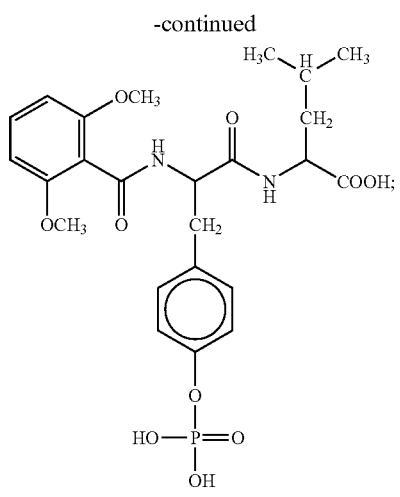
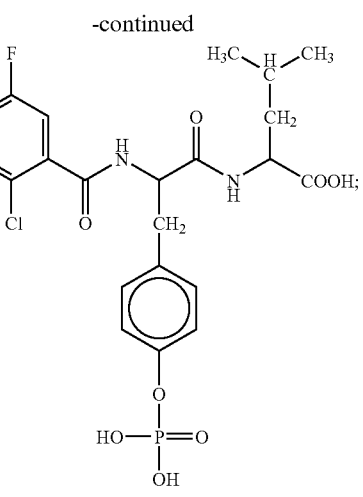
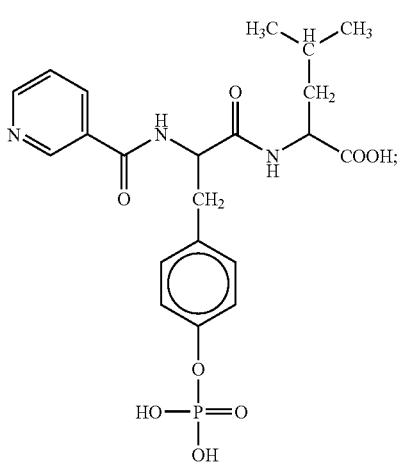
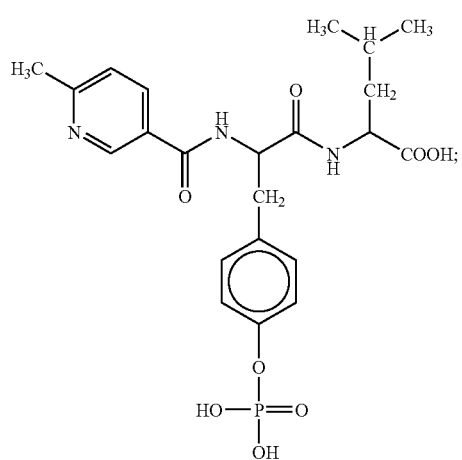
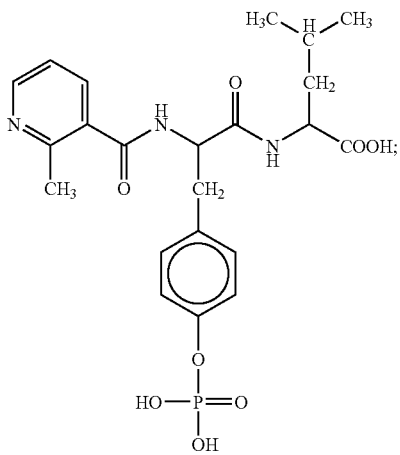
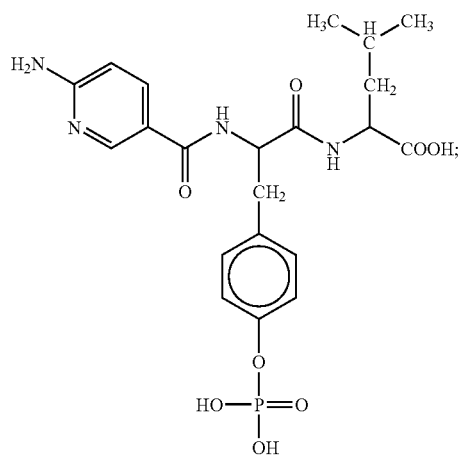

-continued
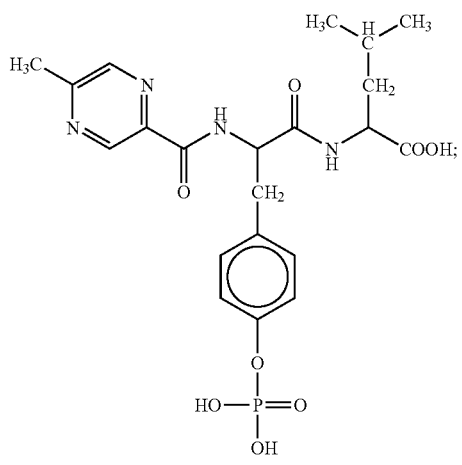
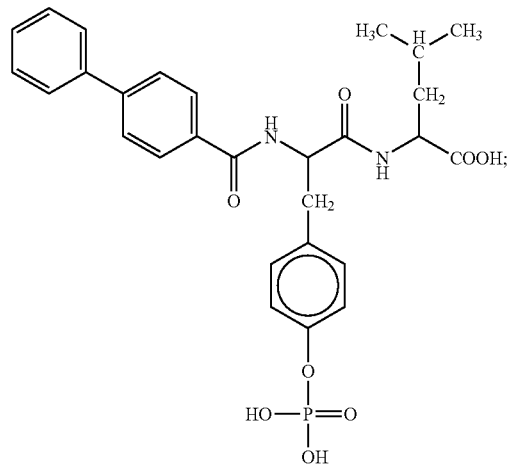
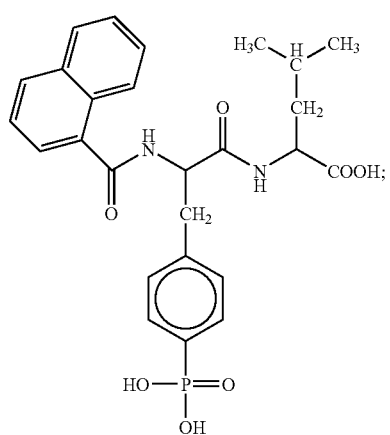
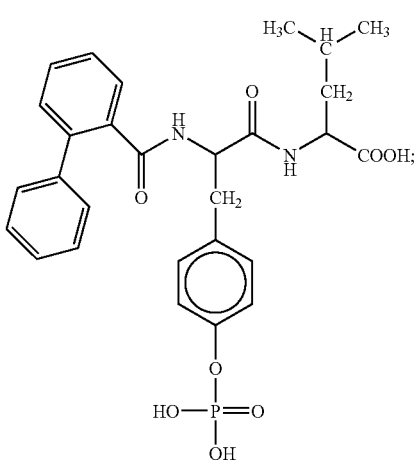
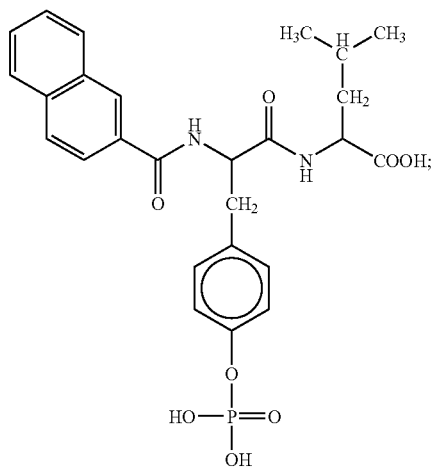
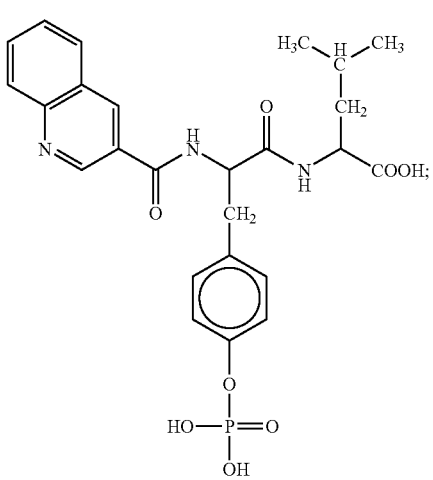
and -continued

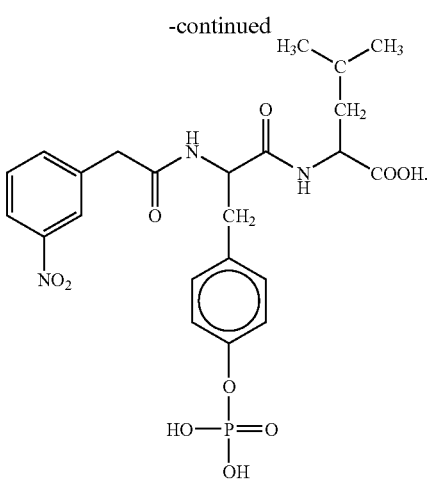

3. The method according to claim 1, wherein $R^1$ is aryl optionally substituted with one or more halogen, —CN, —NO$_2$, —NH$_2$, —CH$_3$, or —OCH$_3$.

4. The method according to claim 3, wherein said one or more halogen is, independently, Cl or F.

5. The method according to claim 1, wherein $R^1$ is phenyl substituted with one or more halogen, —CN, —NO$_2$, —NH$_2$, —CH$_3$, or —OCH$_3$.

6. The method according to claim 5, wherein said one or more halogen is, independently, Cl or F.

7. The method according to claim 1, wherein $R^1$ is heteroaryl optionally substituted with one or more halogen, —CN, —NO$_2$, —NH$_2$, —CH$_3$, or —OCH$_3$.

8. The method according to claim 7, wherein said one or more halogen is, independently, Cl or F.

9. The method according to claim 1, wherein said composition comprises a pharmaceutically acceptable carrier or diluent.

10. A method for inhibiting growth or replication, or inducing apoptosis in a target cell having aberrant or constitutive expression of Stat3, said method comprising contacting the target cell with a composition comprising a peptidomimetic having the formula:

$$R^1Y^*L$$

wherein $R^1$ is selected from the group consisting of alkoxy, cycloalkyl, cycloalkoxy, aryl, aryloxy, alkylcarbonyl, alkoxycarbonyl, cycloalkylcarbonyl, heteroalkyl, heterocycloalkylcarbonyl, heteroaryl, arylcarbonyl, heteroarylcarbonyl, aryloxycarbonyl, heteroaryloxycarbonyl, heterocycloalkoxy, or heterocycloalkoxycarbonyl, any of which can be optionally substituted with one or more of the following: any halogen, —CN, —COOH, =O, —OH, —NO$_2$, —NH$_2$, —N-alkyl, alkyl, alkoxy, cycloalkyl, cycloalkoxy, aryl, aryloxy, alkylcarbonyl, alkoxycarbonyl, cycloalkylcarbonyl, heteroalkyl, heterocycloalkyl, heterocycloalkylcarbonyl, heteroaryl, arylcarbonyl, heteroarylcarbonyl, aryloxycarbonyl, heteroaryloxycarbonyl, heterocycloalkoxy, and heterocycloalkoxycarbonyl;

$Y^*$ is phosphotyrosine;

L is leucine, or another non-polar amino acid;

or a salt thereof.

11. The method according to claim 10, wherein L is alanine or valine.

12. The method according to claim 1, wherein said target cell is a tumor cell, cancer cell, or transformed cell.

13. The method according to claim 1, wherein said target cell is a mammalian cell.

14. The method according to claim 1, wherein said target cell is a human cell.

15. The method according to claim 10, wherein said target cell is a tumor cell, cancer cell, or transformed cell.

16. The method according to claim 10, wherein said target cell is a mammalian cell.

17. The method according to claim 10, wherein said target cell is a human cell.

* * * * *

UNITED STATES PATENT AND TRADEMARK OFFICE
CERTIFICATE OF CORRECTION

PATENT NO. : 7,842,671 B1  
APPLICATION NO. : 11/986237  
DATED : November 30, 2010  
INVENTOR(S) : James Turkson et al.

Page 1 of 2

It is certified that error appears in the above-identified patent and that said Letters Patent is hereby corrected as shown below:

Column 10,  
Lines 5-6, "PY*LKTK-AAVLLPVLLAAP (SEQ ID NO. 1) and PYLKTK-AAVLLPVLLAAP" should read --PY*LKTK-<u>AAVLLPVLLAAP</u> (SEQ ID NO. 1) and PYLKTK-<u>AAVLLPVLLAAP</u>--.  
Line 52, "mM NaF" should read --20 mM NaF--.

Column 27,  
Line 39,

"

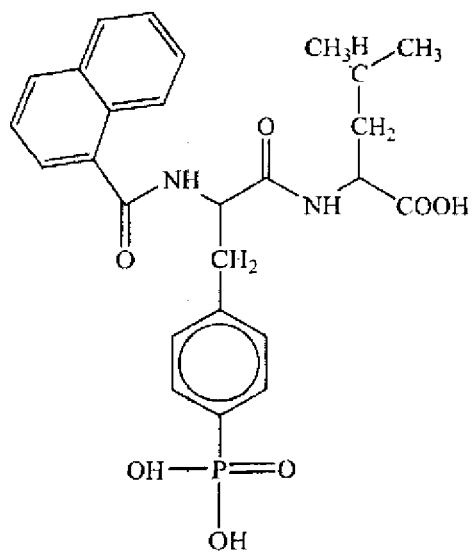

"                     should read

Signed and Sealed this  
Fifteenth Day of March, 2011

David J. Kappos  
*Director of the United States Patent and Trademark Office*

--
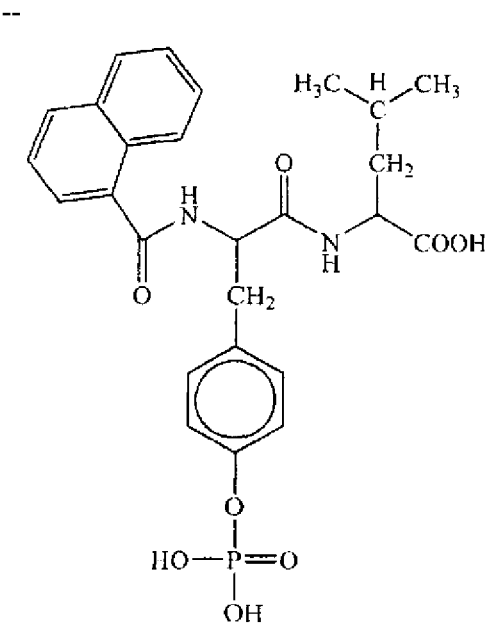
--.